US009040726B2

(12) United States Patent
Wang et al.

(10) Patent No.: US 9,040,726 B2
(45) Date of Patent: May 26, 2015

(54) PROCESS FOR THE PREPARATION OF QUATERNARY N-ALKYL MORPHINAN ALKALOID SALTS

(75) Inventors: Peter X. Wang, Clarkson Valley, MO (US); Gary L. Cantrell, Troy, IL (US); Robert E. Halvachs, Belleville, IL (US); Kevin R. Roesch, Ofallon, IL (US); Henry J. Buehler, St. Louis, MO (US); Joseph P. Haar, Edwardsville, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 672 days.

(21) Appl. No.: 12/553,144

(22) Filed: Sep. 3, 2009

(65) Prior Publication Data

US 2010/0035910 A1   Feb. 11, 2010

(51) Int. Cl.
*C07D 495/00* (2006.01)
*C07D 307/77* (2006.01)
*C07D 489/02* (2006.01)

(52) U.S. Cl.
CPC ................................... *C07D 489/02* (2013.01)

(58) Field of Classification Search
USPC .................. 549/46, 44, 456, 457; 546/46, 44
See application file for complete search history.

(56) References Cited

U.S. PATENT DOCUMENTS

| 3,101,339 | A | 8/1963 | Zeile et al. |
| 4,141,897 | A | 2/1979 | Olofson et al. |
| 4,176,186 | A | 11/1979 | Goldberg et al. |
| 4,322,426 | A | 3/1982 | Hermann et al. |
| 4,368,326 | A | 1/1983 | Rice |
| 4,410,700 | A | 10/1983 | Rice |
| 4,521,601 | A | 6/1985 | Rice |
| 4,535,157 | A | 8/1985 | Meltzer et al. |
| 4,556,712 | A | 12/1985 | Rice |
| 4,613,668 | A | 9/1986 | Rice |
| 4,727,146 | A | 2/1988 | Rice |
| 4,794,186 | A | 12/1988 | Oine et al. |
| 5,112,975 | A | 5/1992 | Wallace |
| 5,240,933 | A | 8/1993 | Merz et al. |
| 5,352,680 | A | 10/1994 | Portoghese et al. |
| 5,574,159 | A | 11/1996 | Chang et al. |
| 5,668,285 | A | 9/1997 | Rice et al. |
| 5,869,669 | A | 2/1999 | Huang et al. |
| 5,907,069 | A | 5/1999 | Becnel et al. |
| 5,922,876 | A | 7/1999 | Huang et al. |
| 5,948,788 | A | 9/1999 | Huang et al. |
| 5,952,495 | A | 9/1999 | Huang et al. |
| 5,981,474 | A | 11/1999 | Manning et al. |
| 6,008,354 | A | 12/1999 | Huang et al. |
| 6,008,355 | A | 12/1999 | Huang et al. |
| 6,013,796 | A | 1/2000 | Huang et al. |
| 6,136,817 | A | 10/2000 | Schmidhammer |
| 6,174,891 | B1 | 1/2001 | Nagase et al. |
| 6,365,742 | B1 | 4/2002 | Mudryk et al. |
| 7,285,665 | B2 * | 10/2007 | Cantrell et al. .................. 546/44 |
| 7,985,858 | B2 * | 7/2011 | Grote et al. ...................... 546/46 |
| 2005/0182258 | A1 | 8/2005 | Schmidhammer et al. |
| 2007/0265293 | A1 | 11/2007 | Boyd et al. |
| 2008/0064712 | A1 | 3/2008 | Schmidhammer et al. |
| 2008/0146804 | A1 | 6/2008 | Stumpf |
| 2008/0207906 | A1 | 8/2008 | Wang et al. |
| 2009/0270624 | A1 | 10/2009 | Weigl et al. |

FOREIGN PATENT DOCUMENTS

| EP | 0 028 959 | 1/1985 |
| ES | 2 121 554 | 11/1998 |
| PL | 124 001 | 7/1985 |
| WO | WO 01/55117 | 8/2001 |
| WO | WO 2004/029059 | 4/2004 |
| WO | WO 2004/043964 | 5/2004 |
| WO | WO 2006/127899 | 11/2006 |

OTHER PUBLICATIONS

Zubrick et al. The Organic Chem Lab Survival Manual, 1984, Chapter 10, p. 91-94.*
Amaravathi et al., "Oxidation of 1-benzyl-3,4-dihydroisoquinolines using active manganese dioxide," Indian Journal of Chemistry, Section B: Organic Chemistry Including Medicinal Chemistry (1983), 22B(12), 1246-7.
Andreu et al., "An efficient method for the preparation of antitumoral α-keto-imines benzyldihydroisoquinolines by selective benzylic oxidation with C/Pd in acetonitrile," Tetrahedron Letters (2002), 43(5), 757-759.
Archer et al., "1-Acetamido-17-carbomethoxydihydrothebainone," Journal of Heterocyclic Chemistry (1981), 18(2), 357-61.
Baxendale et al., "Enantioselective synthesis of the tetrahydrobenzylisoquinoline alkaloid (-)-norarmepavine using polymer supported reagents," Heterocycles (2003), 60(12), 2707-2715.
Benosman et al., "Synthesis of isoquinolines isolated fro Aniba canelilla", Comptes Rendus de l'Academie des Sciences, Serie II:Mecanique, Physique, Chimie, Sciences de la Terre et de l'Univers, 19983, 316(4), pp. 465-468 (French Language).
Bentley et al., The Reduction of Thebaine and Dihydrothebaine by Sodium and Ammonia, Journal of the Chemical Society, Abstracts (1952), pp. 958-966.
Bermejo et al., "Syntheses and antitumor targeting G1 phase of the cell cycle . . . ", Journal of Medicinal Chemistry, 2002, 45(23), pp. 5058-5068.
Beyerman et al., Recl. Trav. Chim. Pays-Bas., 1976, 95, pp. 184.
Bhakuni et al., "Sunthesis of (±)-12-amino derivatives of scoulerine, . . . ", Indian Journal of Chemistry, Section B: Organic chemistry Including Medicinal Chemistry, 1985, 24B(6), pp. 596-601.
Bhakuni et al., "Studies on mannich reaction of 1-benzyltetrahydroisoquinolines", Journal of the Indian Chemical Society, 1988, 65(6), pp. 417-421.
Bjorklund et al., "Cryptic Stereochemistry of Berberine alkaloid biosynthesis", Journal of the American Chemical Society, 1995, 117(5), pp. 1533-1545.

(Continued)

*Primary Examiner* — Andrew D Kosar
*Assistant Examiner* — Raymond Covington
(74) *Attorney, Agent, or Firm* — Mallinckrodt LLC

(57) ABSTRACT

An improved process for the N-alkylation of tertiary morphinan alkaloid bases to form the corresponding quaternary morphinan alkaloid derivatives.

9 Claims, No Drawings

(56) References Cited

OTHER PUBLICATIONS

Boehme et al., "Analogs of M4 selective synthetic muscarinic receptor antagonists: . . . ", Medicinal Chemistry Research, 2002, 11(8), pp. 423-433.
Bognar et al., "Selective Quaternization in the Morphine Series", Tetrahedron Letters, 1964, No. 39, pp. 2867-2871.
Cave et al., "Alkaloids of cryptocarya phyllostemon", Australian Journal of Chemistry, 1989, 42(12), pp. 2243-2263.
Chackalamannil et al., "The synthesis of erythro- and threo-N-methyl-7-hydroxy-1,2,9,10-tetramethoxyaporphine", Tetrahedron Letters, 1980, 21(21), pp. 2029-2032.
Chazerain, "1-Benzoylisoquinolines and their transformation into 1-phenyl-3-benzazepines", Ann. Chim. (Paris), 1963, 8, pp. 255-284.
Cho et al., "Synthesis of 6,7-dimethoxy-1-halobenzy1-1,2,3,4-tetrahydroisoquinolines," Journal of Heterocyclic Chemistry (1999), 36(5), 1151-1156.
Chrzanowska et al., "Asymmetric synthesis of isoquinoline alkaloids," Chemical Reviews (2004), 104, 3341-3370.
Chrzanowska et al., "Synthesis of (S)-(−)-and (R)-(+)-O-methylbharatamine using a diastereoselective Pomeranz-Fritsch-Bobbitt methodology," Tetrahedron: Asymmetry (2005), 16(17), 2954-2958.
Coutts et al., "The enzymatic oxidation of phenolic tetrahydroisoquinoline-1-carboxylic acids," Journal of the Chemical Society, Perkin Transactions 1: Organic and Bio-Organic Chemistry (1972-1999) (1979), (11), 2744-50.
Crooks et al., "Opiate receptor binding properties of morphine-, dihydromorphine-, and codeine 6-0-sulfate ester congeners", Bioorganic & Medicinal Chemistry Letters, 16, 2006, pp. 4291-4295.
Czarnocki, "Enantioselective syntheis of (R)-(−)-calycotomine and (S)-(−)-xylopinine from D-ribonolactone" , Journal of Chemical Research, Synopses, 1992, 10, pp. 334-335.
Czarnocki et al., "Asymmetric synthesis of isoquinoline alkaloids. (R)-and (S)-2-(ethoxycarbonyl)-1-formyl-6, . . . ", bulletin des Societes Chimiques Belges, 1986, 95(9-10), pp. 749-770.
Davis et al., "Synthesis of the orotoberberine alkaloid (S)-(−)-xylopinine using enantiopure sulfinimines", Journal of Organic Chemistry, 2002, 67(4), pp. 1290-1296.
Degraw et al., J. Het. Chem., Jun. 1974, pp. 363.
Fry et al., Mannich Derivatives of Analgesic Agents, Journal of Organic Chemistry (1959), 24, pp. 116-117.
Funke et al., A$^1$H and $^{13}$C Nuclear Magnetic Resonance Study of Three Quaternary Salts of Naloxone and Oxymorphone, J. Chem. Soc. Perkin Trans. (1986) 2, pp. 735-738.
Giger et al., Synthesis and Reactions of the diels-Alder Adduct of Thebaine with 4-phenyl-1,2,4-triazoline-3,5-dione, Tetrahedron (1973), 29(16), pp. 2387-2391.
Gupta et al., "Synthetic photochemistry: Synthesis of liriodenine," Indian Journal of Chemistry, Section B: Organic Chemistry Including Medicinal Chemistry (1983), 22B(5), 429-31.
Hanaoka et al., "Chemical transformation of protoberberines. VIII. A novel synthesis of (t)- fumaricine and a formal synthesis of (±)-alpinigenine," Chemical and Pharmaceutical Bulletin (1985), 33(6), 2273-80.
Hirai et al., "A new preparation of an ochotensin-type isoquinoline by photolysis," Heterocycles (1984), 22(6), 1359-62.
Hu et al., "Photosynthesis of tetrahydroprotoberberines with electron-withdrawing groups on ring D," Chinese Chemical Letters (1998), 9(8), 707-710.
Iorio et al., "Diastereoisomeric Quaternary Morphinium Salts: Synthesis, Stereochemistry and Analgesic Properties", European Journal of Medicinal Chemistry, 1984, 19(1), pp. 11-16.
Kaldor et al., "Stereocontrolled synthesis of cis-dibenzoquinolizine chlorofumarates: curare-like agents of ultrashort duration," Journal of Organic Chemistry (2001), 66(10), 3495-3501.
Kametani et al., "Studies on the syntheses of heterocyclic compounds. DCXCII. A novel synthetic route to phthalideisoquinoline and spirobenzylisoquinoline type alkaloids," Chemical and Pharmaceutical Bulletin (1977), 25(2), 321-6.
Kametani et al., "Studies on the syntheses of heterocyclic compounds. DCXCII. A stereoselective Total Synthesis of (±)-Ophiocarpine; a Simple Route to 13-Hydroxyberbines", JCS Perkin I, 1977, pp. 376-382.
Kametani et al., "Studies on the syntheses of heterocyclic compounds. DCXCIII. A total synthesis of atheroline by photolysis," Tetrahedron (1977), 33(9), 1069-71.
Kametani et al., "Synthesis of oxoaporphine by photolysis. Total synthesis of atheroline," Heterocycles (1975), 3(10), 821-5.
Kapadia et al., "Facile oxidative formation of O-methylvelucryptine during synthesis of dl-O-methylarmepavine," Indian Journal of Pharmaceutical Sciences (1992), 54(6), 227-33.
Kessar et al., "Synthetic Photochemistry: Synthesis of (±)-oliveridine," Indian Journal of Chemistry, Section B: Organic Chemistry Including Medicinal Chemistry (1983), 22B(4), 321-4.
Koczka et al., Selective Quaternization of Compounds with Morphine Skeleton, Acta. Chim. Acad. Sci. Hung. (1967), 51(4), pp. 393-402.
Kunitomo et al., "Synthesis of a few trimethoxyoxoaporphines," Yakugaku Zasshi (1979), 99(1), 102-5. (Japanese language).
Kuo et al., "Antiplatelet activity of benzylisoquinoline derivatives oxidized by cerium (IV) ammonium nitrate," Bioorganic and Medicinal Chemistry Letters (2003), 13(16), 2789-2793.
Lebceuf et al., "Velucryptine, A new isoquinoline alkaloid from cryptocarya velutinosa," Journal of Natural Products (1989), 52(3), 516-21.
Lenz et al., "Lead tetraacetate mediated oxidation of the enamides derived from 1-benzy1-3,4-dihydroisoquinolines," Journal of Organic Chemistry (1988), 53(6), 1176-83.
Lenz et al., "Synthesis of the novel isoquinoline enamide alkaloid polycarpine," Journal of Heterocyclic Chemistry (1981), 18(4), 691-3.
Lopez et al., Photoxidation of Thebaine. A Route to 14-Hydroxymorphinones and Hydrodibenzofuran Analogs of Methadone, Tetrahedron Letters (1994), 35(31), pp. 5727-5730.
Lopez et al., The [4+2] Addition of Singlet Oxygen to Thebaine: New Access to Highly Functionalized Morphine Derivatives via Opioid Endoperoxides, J. Org. Chem. (2000), 65(15), pp. 4671-4678.
Manoharan et al., "Convenient Method for Replacement of Tertiary N-Methyl by Other Alkyl Groups: Application to Morphine Alkaloids", Indian Journal of Chemistry, 1984, vol. 19, No. 1, pp. 5-11.
Manoharan et al., Stereoselectivity in Quaternization of Thebaine: 270 MHz PMR Spectroscopic Studies, Indian Journal of Chemistry, Section B: Organic Chemistry Including Medicinal chemistry (1987), 26B(2), pp. 140-142.
Markaryan et al., "Isoquinoline derivatives. XI. Synthesis and pharmacological activity of 1-arylalky1-4-spirocyclohexane-6,7-dimethoxy-1,2,3,4-tetrahydroisoquinolines and some of their derivatives," Armyanskii Khimicheskii Zhurnal (1975), 28(10), 829-35. (Russian language).
Martin et al., "Oxidation of imines by selenium dioxide," Zeitschrift fuer Naturforschung, Teil B: Anorganische Chemie, Organische Chemie (1986), 41B(10), 1260-4.
Martin et al., "Regiospecific oxidation of substituted 1-benzyl-3,4-dihydroisoquinolines using singlet oxygen," Tetrahedron Letters (1980), 21(27), 2613-16.
Martin et al., "Synthesis and photooxygenation of some substituted 1-benzyl-3,4-dihydroisoquinolines. Mechanism of enamine photooxygenation," Helvetica Chimica Acta (1982), 65(3), 762-74.
McMahon et al., "Rearrangement of 1-(α-hydroxybenzyl)-1,2,3,4-tetrahydroisoquinolines to 1-phenyl-2,3,4,5-tetrahydro-1H-3-benzazepines," Journal of the Chemical Society, Perkin Transactions 1: Organic and Bio-Organic Chemistry (1972-1999) (1982), (9), 2163-7.
Memetzidis et al., "Synthesis of aromatic chloroberbines," Heterocycles (1990), 31(2), 341-51.
Meuzelaar et al., "Chemistry of opium alkaloids. Part 45. Improvements in the total synthesis of morphine," European Journal of Organic Chemistry (1999), 2315-2321.
Meyers et al., "Asymmetric synthesis of isoquinoline alkaloids", Tetrahedron, 1987, 43(21), pp. 5095-5108.

(56) References Cited

OTHER PUBLICATIONS

Meyers et al., "High enantioselective alkyation of tetrahydroisoquinolines with a chiral valinol derivative . . . ", Angewandte Chemie, 1984, 16(6), pp. 448-449.

Miller et al., "Synthesis and biological evaluation of fragmented derivatives of tetrahydroisoquinolines. 2. Trimetoquinol studies", Journal of Medicinal Chemistry, 1975, 18(5), pp. 454-457.

Mujahidin et al., "Enantioselective synthesis of (+)-(S)-laudanosine and (−)-(S)-xylopinine," European Journal of Organic Chemistry (2005), 2689-2693.

Musich et al., Reaction of O-methyl-N, $N^1$-Diisopropylisourea with Amino Acids and Amines, Journal of Organic Chemistry (1977), 42(1), pp. 139-141.

Nagata et al., Synthetic Studies on Isoquinoline Alkaloids. I. An Efficient Synthesis of 9,10-Substituted Protoberberine Alkaloids 1, Chem. Pharm. Bull., 23(11), 1975, pp. 2867-2877.

Naito et al., "Asymmetric synthesis of dibenzo[a,g]quinolizines related to protoberberine alkaloids," Heterocycles (1983), 20(5), 779-82.

Naito et al., "Reductive photocyclization of enamides and its application to alkaloid synthesis", Kobe Women's Coll. Pharm., Tennen Yuki Kagobutsu Toronkai Koen Yoshishu, $24^{th}$, 1981, pp. 460-465.

Naito et al., "Reductive photocyclization of enamide in the presence of a chrial metal hydride complex . . . ", Kobe Women's Coll. Pharm., Heterocycles, 1981, 16(7), pp. 1141-1143.

Ninan et al., "An Improved Synthesis of Noroxymorphone", Tetrahedron, 48(32), 1992, pp. 6709-6716.

Orito et al., "Aryl radical cyclizations of 1-(2'-Bromobenzyl)isoquinolines with AIBN-Bu3SnH: Formation of aporphines and Indolo[2,1-a]isoquinolines," Organic Letters (2000), 2(3), 307-310.

Orito et al., "New synthesis of phthalideisoquinoline alkaloids via a stereoselective hydride reduction of 1-(2'-bromobenzoyl)-3,4-dihydroisoquinoline methiodide, followed by palladium-catalyzed carbonylation aided by chlorotrimethylsilane," Synlett (1994), (4), 245-6.

Orito et al., "Synthesis of (±)-norcoralydine and (±)-tetrahydropalmatine," Organic Preparations and Procedures International (1989), 21(3), 309-14.

Orito et al., "Synthesis of phthalideisoquinoline and protoberberine alkaloids and indolo [2,1-a] isoquinolines in a divergent route involving palladium(0)-catalyzed carbonylation," Journal of Organic Chemistry (1999), 64(18), 6583-6596.

Otto et al., Selection and Amplification of Hosts from Dynamic combinatorial Libraries of Macrocyclic Disulfides, Science (Washington, DC, United States) (2002), 297(5581), pp. 590-593 & Supporting Online Material.

Rice, "Synthetic Opium Alkaloids and Derivatives. A Short total Synthesis . . . ", J. Org. Chem., 1980, 45, pp. 3135-3137.

Rozwadowska et al., "Mammalian alkaloids: O-methylation of (S)- and (R)-dideoxynorlaudanosoline-1-carboxylic acid by catechol O-methyltransferase and identification of a yellow pigment obtained at physiological pH," Helvetica Chimica Acta (1988), 71(7), 1598-607.

Schultz et al., Thebaine Cyclopropanation, Russian Journal of Organic chemistry (Translation of Zhurnal Organicheskoi Khimii) (2003), 39(8), pp. 1083-1088.

Seki, Isao, Studies on the Morphine Alkaloids and its Related Compounds. XIV. Preparation of 6-Amino-hydrophenanthrene Compounds from Hofmann Degradation Products of the Morphine Alkaloids, Chemical & Pharmaceutical Bulletin (1966), 14(5), pp. 453-461.

Shklyaev et al., "A new approach to synthesis of 3,3-dialkyl-3,4-dihydroisoquinoline derivatives," Heteroatom Chemistry (2004), 15(7), 486-493.

Shults et al., Tranformations of Quaternary Tetrahydrothebaine Sulfones, Zh. Org. Khim. (1993), 29(6), pp. 1149-1162, (English pp. 953-963).

Simanek et al., "Synthesis of hypecorine and hypecorinine analogs from 3,4-dihydropapaverine," Symp. Pap. IUPAC Int. Symp. Chem. Nat. Prod., 11th (1978), vol. 2, 58-60.

Simanek et al., "Isolation and chemistry of alkaloids from some plants of the family Papaveraceae. Part LXXIV. Synthesis of hypecorine and hypecorinine analogs from 3,4-dihydropapaverine", Heterocycles, 1978, 9(9), pp. 1233-1240.

Sladkov et al., "2,3,10,11-Tetramethoxy-5,6,7,8,13,13a-hexahydroprotoberberines and their B-seco analogs: Synthesis and antineoplastic activity," Khimiko-Farmatsevticheskii Zhurnal (1989), 23(1), 50-3. (Russian language).

Sladkov et al., "Benzophenanthridines. VI. Conversions of protoberberine alkaloids into benzo[c]phenanthridines. Hofmann degradation of α-N-and β-N-methyl-(±)-13αhydroxyxylopinine iodides," Zhurnal Organicheskoi Khimii (1989), 25(4), 854-62 (Russian language).

Tolkachev et al., "Application of the Willgerodt-Kindler reaction in the synthesis of the 1-benzyl-1,2,3,4-tetrahydroisoquinoline alkaloids and their derivatives," Symp. Pap. IUPAC Int. Symp. Chem. Nat. Prod., 11th (1978), vol. 3, 47-50.

Trifonov et al., "Application of organic photochemistry in the synthesis of (±)-glaucine," Izvestiya po Khimiya (1978), 11(2), 297-304.

Trifonov et al., "Berbin-8-ones from 2'-halo-l-benzylisoquinolines and metal carbonyls," Tetrahedron Letters (1985), 26(26), 3159-62.

Uematsu et al., "Asymmetric transfer hydrogenation of imines," Journal of the American Chemical Society (1996), 118, 4916-4917.

Walterova et al., "Isolation and chemistry of the alkaloids from some plants of the genus *Papaver*. LXXVII. Pseudobase formation in 2-methylpapaverinium cations and their biotransformation by enzymes of rat liver homogenates in vitro," Collection of Czechoslovak Chemical Communications (1980), 45(3), 956-65.

Wert et al., "Hofmann degradation of (β-hydroxy ammonium salts. α- and β-hydroxylaudanosine, 7-hydroxyglaucine, and 13-hydroxyxylopinine," Journal of Organic Chemistry (1982), 47(26), 5141-50.

Williams et al., "One-pot formation of nitrogen-containing heterocyclic ring systems using a deprotection-cyclization-asymmetric reduction sequence," Chemical Communications Cambridge, United Kingdom) (2005), (37), 4735-4737.

Yamada et al., "Studies on 1,2,3,4-tetrahydroisoquinolines. VI. Reutilization of the unwanted (R)-isomer of (S)-(−)-5,7-dihydroxy-1-(3,4,5-trimethoxybenzyl)-1,2,3,4-tetrahydroisoquinoline (TA-073)," Chemical and Pharmaceutical Bulletin (1983), 31(1), 70-4.

Zhao et al., "Synthesis of nitrones from 3,4-dihydroisoquinoline derivatives by oxidation with m-chloroperoxybenzoic acid," Organic Preparations and Procedures International (1997), 29(2), 185-194.

* cited by examiner

PROCESS FOR THE PREPARATION OF QUATERNARY N-ALKYL MORPHINAN ALKALOID SALTS

CROSS REFERENCE TO RELATED APPLICATIONS

This application is a continuation of PCT/US2008/003070, filed Mar. 6, 2008, which claims the benefit of U.S. Provisional Application No. 60/893,163 filed Mar. 6, 2007 and U.S. Provisional Application No. 60/953,248 filed Aug. 1, 2007

FIELD OF THE INVENTION

The present invention generally relates to improved processes for the synthesis of quaternary N-alkyl salts of morphinan alkaloids such as naltrexone methobromide.

BACKGROUND OF THE INVENTION

N-methyl quaternary derivatives of morphinan alkaloids such as naltrexone ((5α)-17-(cyclopropylmethyl)-4,5-epoxy-3,14-dihydroxymorphinan-6-one sometimes referred to as N-cyclopropylmethyl-noroxymorphone) and naloxone ((5α)-4,5-epoxy-3,14-dihydroxy-17-(2-propenyl)morphinan-6-one sometimes referred to as N-allyl-noroxymorphone) have useful pharmacological properties as potent antagonists of the mu receptor. They bind to peripheral receptors primarily located in the gastrointestinal tract, act as antagonists and effectively mitigate some of the undesirable side effects of opiate therapy such as constipation and nausea. Because of their ionic charge, however, they do not traverse the blood brain barrier into the central nervous system; hence, the central activity of opiates responsible for pain relief is not blocked in the presence of these quaternary derivatives.

In U.S. Pat. No. 4,176,186, Goldberg et al. generally describe the preparation of quaternary derivatives of certain morphinan alkaloids by quaternizing a tertiary N-substituted morphinan alkaloid with a methylating agent such as methyl bromide, methyl iodide or dimethyl sulfate. Goldberg et al. disclose that the methylating agent itself may be used as the solvent or, alternatively, another solvent medium such as methanol, ethanol, or other alcohols, methylene chloride, chloroform tetrahydrofuran, dioxane, dimethylformamide, dimethyl sulfoxide, acetonitrile, nitromethane or hexamethylphosphoric triamide may be used. Goldberg et al. state that they especially prefer acetone because the product precipitates in pure crystalline form during the reaction, and in their Example 5, they dissolve N-cyclopropylmethylnoroxymorphone in a mixture consisting of 50 mL of absolute acetone and 0.5 mL of dimethylformamide and then admix the resulting solution with methyl bromide. Methyl bromide was used in excess, greater than six-fold molar excess relative to the free base, over a period of 3 weeks in a pressure vessel.

In WO 2004/043964, Cantrell et al. disclose a process for the synthesis of naltrexone methobromide. For example, 100 g of naltrexone base was reacted with methyl bromide (MeBr) in 1-methylpyrrolidinone (NMP) at 61 to 65° C. to provide 85 g of a crude naltrexone methobromide in approximately 60 mol. % yield of approximately 90% pure naltrexone methobromide (see Example 1). Purification of the crude product was carried out in three steps to give pure naltrexone methobromide; in addition, 20% of unreacted naltrexone was disposed of in the waste streams, a significant loss. While this process constitutes significant progress in the synthesis of naltrexone methobromide and other quaternary morphinan alkaloids, a need remains for yet further improvement.

In WO 2006/127899, Doshan et al. disclose a stereoselective synthesis of the R-isomer of naltrexone methobromide by quaternization of a 3-O-protected-naltrexone with a methylating agent followed by removal of the protecting group. N-methylation of tertiary morphinan alkaloids has been shown in a previously published NMR study to be highly stereoselective yielding the R-isomer; (see Funke and de Graaf, J. Chem. Soc., Perkins Trans. II, 1985, 385.). In the synthesis disclosed by Doshan et al (Example 2), 3-O-isobutyryl-naltrexone was reacted with a 4-fold excess of methyl iodide in a sealed glass pressure vessel in a nitrogen atmosphere at 88 to 90° C. for 17 hrs. The vessel was then cooled to ambient temperature and evacuated to remove unreacted methyl iodide. The product, 3-O-isobutyryl-methylnaltrexone iodide, a white solid, was dissolved in a minimum volume of dichloromethane/methanol (4:1) and purified by silica gel chromatography. The 3-O-protecting group was removed by reaction with 48% HBr at 64 to 65° C. for 6.5 hours and the mixture was concentrated to an oil by rotary evaporation at 22 to 25° C. Purification of the crude product was carried out by ion exchange on a bromide column and a solid was isolated from selected pooled fractions. Serial recrystallization of the solid from methanol yielded a white product (64% yield). Product analysis showed an isomer distribution of approximately 97% R-isomer and 3% S-isomer. Additional recrystallizations and/or chromatography (Up to 10 times) were required to eliminate the S-isomer. Hence, a need remains for further improvement.

SUMMARY OF THE INVENTION

Among the various aspects of the present invention is an improved process for the preparation and/or recovery of quaternary morphinan alkaloids.

Briefly, therefore, the present invention is directed to a process for the preparation of a quaternary derivative of a tertiary N-substituted morphinan alkaloid, the process comprising: (i) combining a tertiary N-substituted morphinan alkaloid substrate, or a suspension of a tertiary N-substituted morphinan alkaloid substrate in an anhydrous solvent system with an alkylating agent, or a solution of the alkylating agent in the anhydrous solvent system, to form a reaction product mixture containing the quaternary derivative of the tertiary N-substituted morphinan alkaloid substrate and any unreacted tertiary N-substituted morphinan alkaloid substrate, the solvent system comprising an anhydrous aprotic dipolar solvent(s) with the aprotic dipolar solvent(s) constituting at least 25 wt. % of the solvent system; and (ii) adding a non-solubilizing solvent to the reaction product mixture to precipitate the quaternary derivative.

The present invention is further directed to a process for the preparation of a quaternary derivative of a tertiary N-substituted morphinan alkaloid having a C(3) hydroxy substituent, the process comprising: (i) combining a tertiary N-substituted morphinan alkaloid substrate, or a suspension of a tertiary N-substituted morphinan alkaloid substrate in an anhydrous solvent system with an alkylating agent, or a solution of the alkylating agent in the anhydrous solvent system, to form a reaction product mixture containing the quaternary derivative of the tertiary N-substituted morphinan alkaloid substrate and any unreacted tertiary N-substituted morphinan alkaloid substrate, the solvent system comprising an anhydrous aprotic dipolar solvent with the aprotic dipolar solvent constituting at least 25 wt. % of the solvent system, and (ii) adding an acid to the reaction product mixture to suppress ionization of the C(3) hydroxy substituent and production of C(3) alkoxy side products.

The present invention is further directed to a process for the preparation of a quaternary derivative of a tertiary N-substituted morphinan alkaloid, the process comprising adding less than 3 equivalents of an alkylating agent dissolved in an anhydrous dipolar aprotic solvent to a tertiary N-substituted morphinan alkaloid substrate dissolved in an anhydrous solvent system, to form a reaction product mixture containing the quaternary derivative of the tertiary N-substituted morphinan alkaloid substrate and any unreacted tertiary N-substituted morphinan alkaloid substrate, the rate of addition of the alkylating agent being less than 0.02 equivalents of alkylating agent per equivalent of substrate per minute. In addition, the solvent system comprises an aprotic dipolar solvent with the aprotic dipolar solvent constituting at least 25 wt. % of the solvent system, and wherein the solution of the alkylating agent is maintained at a temperature below about 0° C. and is added to the reaction mixture at a temperature of between about 50° C. and about 85° C. so as to limit O-alkylation to less than 10% and inhibit evaporative loss of alkylating agent.

Further still, the present invention is directed to a process for the preparation of a quaternary derivative of a tertiary N-substituted morphinan alkaloid, the process comprising adding less than 3 equivalents of a solution of an alkylating agent dissolved in an anhydrous dipolar aprotic solvent to a tertiary N-substituted morphinan alkaloid substrate dissolved in an anhydrous solvent system, to form a reaction product mixture containing the quaternary derivative of the tertiary N-substituted morphinan alkaloid substrate and any unreacted tertiary N-substituted morphinan alkaloid substrate, the rate of addition of the alkylating agent being less than 0.02 equivalents of alkylating agent per equivalent of substrate per minute based upon the concentration of substrate in the reaction mixture; wherein the solution of the alkylating agent is maintained at a temperature below about 0° C. and is added to the reaction mixture at a temperature of between about 50° C. and about 85° C. so as to inhibit O-alkylation at the C(3) hydroxide to less than 10% and inhibit evaporative loss of alkylating agent.

Further still, the present invention is directed to a process for the preparation of a quaternary derivative of a tertiary N-substituted morphinan alkaloid having a protected C(3) hydroxy substituent, the process comprising (i) combining the C(3)-O-protected tertiary N-substituted morphinan alkaloid substrate, or a suspension of the C(3)-O-protected tertiary N-substituted morphinan alkaloid substrate in an anhydrous solvent system, with an alkylating agent, or a solution of the alkylating agent in the anhydrous solvent system, at a pressure of less than about 2 atmospheres, to form a reaction product mixture containing the quaternary derivative of the C(3)-O-protected tertiary N-substituted morphinan alkaloid substrate and any unreacted tertiary C(3)-O-protected N-substituted morphinan alkaloid substrate, the solvent system comprising an anhydrous aprotic dipolar solvent with the aprotic dipolar solvent constituting at least 25 wt. % of the solvent system, and subsequently removing the C(3)-O protecting group.

Further still, the present invention is directed to a process for the preparation of a quaternary derivative of a tertiary N-substituted morphinan alkaloid having a C(3-hydroxy substituent, the process comprising the steps of (i) generating a C(3)-O-protected tertiary morphinan alkaloid by reacting a C(3)-OH-morphinan alkaloid with a protecting agent, PG-L; (ii) isolating the generated C(3)-O-protected tertiary N-substituted morphinan alkaloid; (iii) combining the isolated C(3)-O-protected tertiary N-substituted morphinan alkaloid with an alkylating agent in an anhydrous solvent system to form a reaction product mixture, the reaction product mixture containing a C(3)-O-protected quaternary derivative of the C(3)-O-protected tertiary N-substituted morphinan alkaloid substrate and any unreacted C(3)-O-protected tertiary N-substituted morphinan alkaloid substrate in the anhydrous solvent system, the anhydrous solvent system comprising an aprotic dipolar solvent with the aprotic dipolar solvent constituting at least 25 wt. % of the solvent system; (iv) isolating the C(3)-O-protected quaternary derivative from the reaction product mixture; and (v) removing the protecting group from the isolated C(3)-O-protected quaternary derivative to yield a quaternary derivative of a tertiary N-substituted morphinan alkaloid having a C(3)-hydroxy substituent.

The present invention is also directed to the preparation of a quaternary derivative of a tertiary N-substituted morphinan alkaloid having a C(3)-hydroxy substituent, the process comprising:

(i) forming a C(3)-protected hydroxy derivative of the tertiary N-substituted morphinan alkaloid, comprising:
  (A) treating the tertiary N-substituted morphinan alkaloid with a protecting group precursor in a biphasic first solvent system comprising water and a water immiscible solvent to form a first reaction product mixture comprising the C(3)-protected hydroxy derivative of the tertiary N-substituted morphinan alkaloid and the water immiscible solvent in an organic layer, and protecting group precursor, tertiary N-substituted morphinan alkaloid, and water in an aqueous layer;
  (B) separating the organic layer from the aqueous layer;
  (C) drying the organic layer;
  (D) treating the dried organic layer produced in step (i)(C) with additional protecting group precursor to increase the conversion of tertiary N-substituted morphinan alkaloid to the C(3)-protected hydroxy derivative;
  (E) removing water immiscible solvent from the treated organic layer produced in step (i)(D) to form a concentrate comprising the C(3)-protected hydroxy derivative; and
  (F) dissolving the concentrate produced in step (i)(E) comprising the C(3)-protected hydroxy derivative in an anhydrous solvent system;
(ii) treating the C(3)-protected hydroxy derivative in the anhydrous solvent system of step (i)(F) with an alkylating agent to form a second reaction product mixture comprising the quaternary derivative of the C(3)-protected hydroxy derivative, unreacted alkylating agent, and any unreacted C(3)-protected hydroxy derivative; and
(iii) deprotecting the quaternary derivative of the C(3)-protected hydroxy derivative to form a third reaction product mixture comprising the quaternary derivative of the tertiary N-substituted morphinan alkaloid, the quaternary derivative of the tertiary N-substituted morphinan alkaloid having a C(3)-hydroxy substituent.

Further still, the present invention is directed to a composition comprising R-naltrexone methobromide, S-naltrexone methobromide, the C(3)-O-methyl derivative of naltrexone methobromide, and naltrexone wherein the composition contains at least 70% (w/w) of R-naltrexone methobromide, at least 1% (w/w) of S-naltrexone methobromide, but no more than 0.2% (w/w) of the C(3)-O-methyl derivative of naltrexone methobromide, based upon the combined weight of the R-naltrexone methobromide, S-naltrexone methobromide, C(3)-O-methyl derivative of naltrexone methobromide, and naltrexone in the composition.

Further still, the present invention is directed to a composition comprising R-naltrexone methobromide, S-naltrexone methobromide, the C(3)-O-cyclopropylmethyl derivative of naltrexone methobromide, and oxymorphone wherein the composition contains at least 70% (w/w) of S-naltrexone methobromide, at least 1% (w/w) of R-naltrexone methobromide, but no more than 0.2% (w/w) of the C(3)-O-cyclopropylmethyl derivative of naltrexone methobromide, based upon the combined weight of the R-naltrexone methobromide, S-naltrexone methobromide, C(3)-O-cyclopropylmethyl derivative of naltrexone methobromide, and oxymorphone in the composition.

Other objects and features will be in part apparent and in part pointed out hereinafter.

DETAILED DESCRIPTION OF THE PREFERRED EMBODIMENTS

Among the various aspects of the present invention is an improved process for the N-alkylation of tertiary morphinan alkaloid bases to form a corresponding quaternary morphinan alkaloid derivative. In general, the process comprises combining a tertiary N-substituted morphinan alkaloid substrate with an alkylating agent in an anhydrous solvent system to form the corresponding quaternary derivative. In certain embodiments, the tertiary morphinan alkaloid base possesses a C(3) hydroxy group; in such embodiments, advantageously, undesired C(3)-O-alkylation of this C(3) hydroxy group can be inhibited by including an anhydrous acid in the reaction mixture. Alternatively, or additionally, it has been found that by controlling the rate of addition of the alkylating agent to the reaction mixture, evaporative loss of a volatile alkylating agent such as methyl bromide can be inhibited. Further, the solvent system may alternately or additionally comprise solvents in which the quaternary derivative has less solubility so as to precipitate the quaternary product and also improve flowability and subsequent processing of the product mixture. Still further, the C(3)-hydroxy group may be protected in one or a series of protection reactions to form the C(3)-protected hydroxy derivative of the tertiary morphinan starting material. The reaction product mixtures (or portions thereof) containing the desired compounds and intermediates (e.g., the solvent/organic layer in a biphasic mixture) may be subjected to various wash and extraction steps in order to remove impurities and by-products. In various embodiments in which the C(3)-protected hydroxy derivative is formed, the alkylating agent may be purged from the reaction mixture prior to removal of the C(3)-hydroxy protecting group.

Tertiary Morphinan Alkaloid Bases and Quaternary Products

In one embodiment, the tertiary N-substituted morphinan alkaloid substrate has the structure of Formula 1 and the quaternary derivative has the structure of Formula 1A:

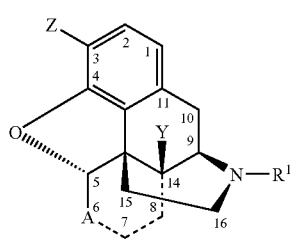

Formula 1

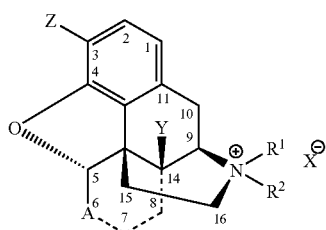

Formula 1A wherein

A is —C(O)—, —C(S)—, —C(=CH$_2$)—, —CH(A$_1$)- or —C(A$_1$)=,

A$_1$ is hydroxy, alkoxy, or acyloxy,

R$^1$ is hydrocarbyl or substituted hydrocarbyl,

R$^2$ is hydrocarbyl or substituted hydrocarbyl,

X$^1$ is a halide, sulfate, sulfonate, fluoroborate, fluorosulfonate, methylsulfate, ethylsulfate, trifluoromethanesulfonate, hexachloroantimonate, hexafluorophosphate, or tetrafluoroborate;

Y, if present, is hydrogen, hydroxy, protected hydroxy, alkoxy, or acyloxy,

Z is hydroxy, protected hydroxy, alkoxy, or acyloxy, and the dashed lines between the carbon atoms at positions 6 and 7, 7 and 8, and 8 and 14, respectively, represent (i) carbon-carbon single bonds, (ii) carbon-carbon single bonds between positions 6 and 7 and between positions 8 and 14, and a double bond between positions 7 and 8, or (iii) conjugated carbon-carbon double bonds between positions 6 and 7 and positions 8 and 14, with the proviso that Y is not present if there is a double bond between the carbons at positions 8 and 14.

In one embodiment, Y and Z are independently protected hydroxy comprising —OCH$_3$, —OAc, —OTHP, —OSiR$_3$, —OBn, —OBz, —OBs, —OTs, or —OMs wherein each R is independently hydrocarbyl.

As previously mentioned, in certain embodiments, the tertiary morphinan alkaloid base possesses a hydroxy group, more specifically a C(3) hydroxy group when the tertiary morphinan alkaloid base corresponds to Formula 1. In this embodiment, the tertiary N-substituted morphinan alkaloid substrate has the structure of Formula 11 and the quaternary derivative has the structure of Formula 11A:

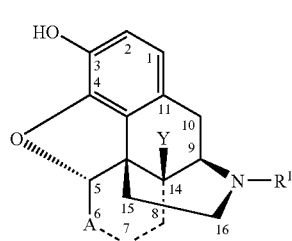

Formula 11

Formula 11A

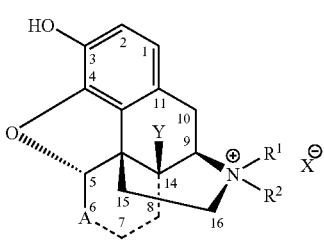

wherein A, A₁, R¹, R², X¹, and Y are as defined in connection with Formulae 1 and 1A.

In one embodiment, the tertiary morphinan alkaloid base is represented by Formula 2 and the product is represented by Formula 2A.

Formula 2

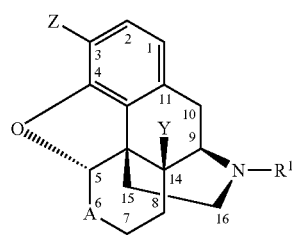

Formula 2A

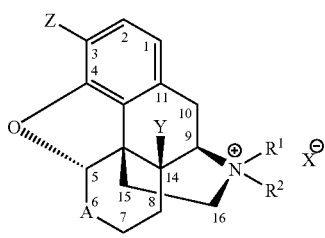

wherein
A is —C(O)—, —C(S)—, —C(=CH₂)—, or —CH(A₁)—,
A₁ is hydroxy, alkoxy, or acyloxy,
R¹ is hydrocarbyl or substituted hydrocarbyl,
R² is hydrocarbyl or substituted hydrocarbyl,
X¹ is a halide, sulfate, sulfonate, fluoroborate, fluorosulfonate, methylsulfate, ethylsulfate, trifluoromethanesulfonate, hexachloroantimonate, hexafluorophosphate, or tetrafluoroborate;
Y is hydrogen, hydroxy, protected hydroxy, alkoxy, or acyloxy, and
Z is hydroxy, protected hydroxy, alkoxy, or acyloxy.

Representative tertiary morphinan alkaloids falling within the scope of Formula 2 include naltrexone ((5α)-17-(cyclopropylmethyl)-4,5-epoxy-3,14-dihydroxymorphinan-6-one), oxymorphone ((5α)-4,5-epoxy-3,14-dihydroxy-17-methylmorphinan-6-one), oxycodone ((5α)-4,5-epoxy-14-hydroxy-3-methoxy-17-methylmorphinan-6-one), hydromorphone ((5α)-4,5-epoxy-3-hydroxy-17-methylmorphinan-6-one), naloxone ((5α)-4,5-epoxy-3,14-dihydroxy-17-(2-propenyl)morphinan-6-one), nalmefene ((5α)-17-(cyclopropylmethyl)-4,5-epoxy-6-methylenemorphinan-3,14-diol) and nalbuphine ((5α)-17-(cyclobutylmethyl)-4,5-epoxymorphinan-3,6,14-triol). Preferred tertiary morphinan alkaloids and quaternary derivatives thereof falling within the scope of Formulae 2 and 2A correspond to Formulae 22 and 22A.

Formula 22

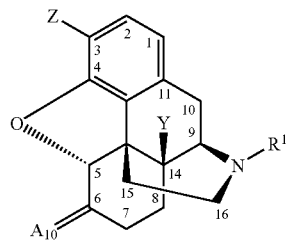

Formula 22A

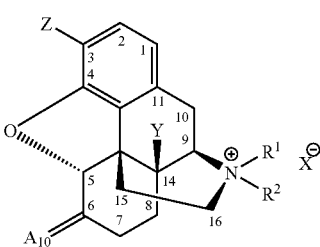

wherein R¹, R², X¹, Y and Z are as defined in connection with Formulae 2 and 2A and A₁₀ is oxygen, sulfur or methylene; in one embodiment, A₁₀ is preferably oxygen or methylene. Tertiary morphinan alkaloids falling within the scope of Formula 22 include naltrexone, oxymorphone, oxycodone, hydromorphone, naloxone, and nalmefene.

Other preferred tertiary morphinan alkaloids and quaternary derivatives thereof falling within the scope of Formulae 2 and 2A correspond to Formulae 222 and 222A.

Formula 222

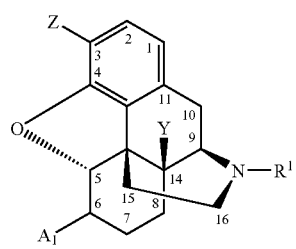

Formula 222A

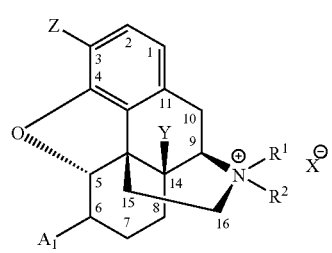

wherein R¹, R², X¹, Y and Z are as defined in connection with Formulae 2 and 2A and A₁ is hydroxy, alkoxy or acyloxy. Tertiary morphinan alkaloids falling within the scope of Formulae 222 include nalbuphine.

In one embodiment, the tertiary morphinan alkaloid base is represented by Formula 3 and the product is represented by Formula 3A.

Formula 3

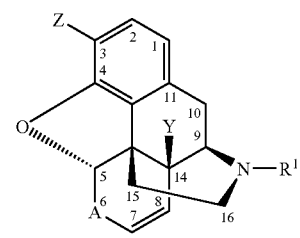

Formula 3A

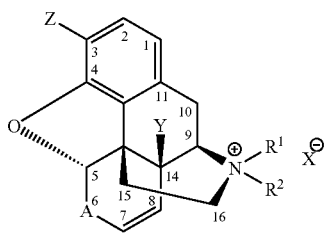

wherein

A is —C(O)—, —C(S)—, —C(=CH$_2$)—, or —CH(A$_1$)—,

A$_1$ is hydroxy, alkoxy, or acyloxy,

R$^1$ is hydrocarbyl or substituted hydrocarbyl,

R$^2$ is hydrocarbyl or substituted hydrocarbyl,

X$^1$ is a halide, sulfate, sulfonate, fluoroborate, fluorosulfonate, methylsulfate, ethylsulfate, trifluoromethanesulfonate, hexachloroantimonate, hexafluorophosphate, or tetrafluoroborate;

Y is hydrogen, hydroxy, protected hydroxy, alkoxy, or acyloxy, and

Z is hydroxy, protected hydroxy, alkoxy, or acyloxy.

Representative tertiary morphinan alkaloids falling within the scope of Formula 3 include morphine ((5α,6α)-7,8-didehydro-4,5-epoxy-17-methylmorphinan-3,6-diol), codeine ((5α,6α)-7,8-didehydro-4,5-epoxy-3-methoxy-17-methylmorphinan-6-ol), codeinone ((5α)-7,8-didehydro-4,5-epoxy-3-methoxy-17-methylmorphinan-6-one), 14-hydroxycodeinone ((5α)-7,8-didehydro-4,5-epoxy-14-hydroxy-3-methoxy-17-methylmorphinan-6-one), 14-hydroxymorphinone ((5α)-7,8-didehydro-4,5-epoxy-3,14-dihydroxy-1,7-methylmorphinan-6-one) and morphinone ((5α)-7,8-didehydro-4,5-epoxy-3-hydroxy-17-methylmorphinan-6-one).

In another embodiment, the tertiary morphinan alkaloid base is represented by Formula 4 and the product is represented by Formula 4A.

Formula 4

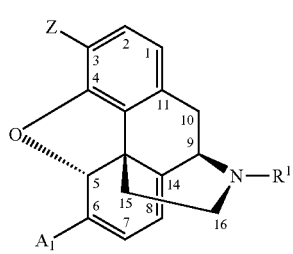

Formula 4A

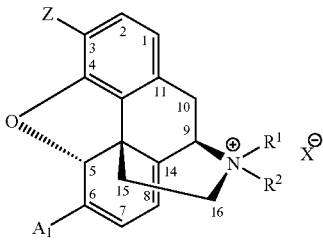

wherein

A$^1$ is hydroxy, alkoxy, or acyloxy,

R$^1$ is hydrocarbyl or substituted hydrocarbyl,

R$^2$ is hydrocarbyl or substituted hydrocarbyl,

X$^1$ is a halide, sulfate, sulfonate, fluoroborate, fluorosulfonate, methylsulfate, ethylsulfate, trifluoromethanesulfonate, hexachloroantimonate, hexafluorophosphate, or tetrafluoroborate, and Z is hydroxy, protected hydroxy, alkoxy, or acyloxy.

Representative tertiary morphinan alkaloids and quaternary derivatives thereof falling within the scope of Formula 4 and Formula 4A, respectively, include thebaine ((5α)-6,7,8,14-tetradehydro-4,5-epoxy-3,6-dimethoxy-17-methylmorphinan) and oripavine ((5α)-6,7,8,14-tetrahydro-4,5-epoxy-6-methoxy-17-methylmorphinan-3-ol).

In each of these embodiments in which a tertiary alkaloid base is alkylated to form the corresponding N-alkyl quaternary alkaloid salt represented by Formula 1A, 2A, 22A, 222A, 3A, or 4A, Z is preferably hydroxy, protected hydroxy, alkoxy or acyloxy, more preferably hydroxy or methoxy. For example, in each of these embodiments Z may be selected from —OCH$_3$, —OAc, —OTHP, —OSiR$_3$ (wherein each R is independently hydrocarbyl, preferably lower alkyl), —OBn, —OBz, —OBs, —OTs, or —OMs. By way of further example, in each of these embodiments, Z may be hydroxy. In each of these embodiments, Y, if present, is preferably hydrogen, hydroxy, protected hydroxy, alkoxy or acyloxy, more preferably hydrogen or hydroxy. For example, in each of these embodiments Y, if present, may be selected from —OCH$_3$, —OAc, —OTHP, —OSiR$_3$ (wherein each R is independently hydrocarbyl, preferably lower alkyl), —OBn, —OBz, —OBs, —OTs, and —OMs. In each of these embodiments, R$^1$ is preferably methyl, ethyl, propyl, allyl (—CH$_2$CH=CH$_2$), chloroallyl, cyclopropylmethyl, cyclobutylmethyl, or propargyl. In each of these embodiments, R$^2$ is preferably alkyl, alkenyl or alkaryl, more preferably lower alkyl, and typically methyl. In each of these embodiments, X$^1$ is preferably bromide.

N-alkylation Reactions

In the process of the present invention, a tertiary N-substituted morphinan alkaloid substrate reacts with an alkylating agent in an anhydrous solvent system to form the corresponding quaternary derivative.

A range of alkylating agents may be used for this purpose. In general, alkylating agents comprising 1 to 8 carbons, optionally substituted and optionally unsaturated are preferred. Typically, the alkylating agent will be an alkyl, allyl, alkallyl, propargyl, or benzyl salt of anions such as halides or optionally substituted sulfates, sulfonates, borates, phosphates, or antimonates. Thus, for example, the alkylating agent may be a methyl, ethyl, propyl, allyl, cyclopropyl, cyclopropylmethyl, propargyl or benzyl salt of an anion such as a halide, sulfate, sulfonate, fluorosulfonate, methylsulfate, ethylsulfate, trifluoromethane-sulfonate, hexachloroantimonate, hexafluorophosphate, or tetrafluoroborate. Representative examples include methyl bromide, cyclopropylmethyl bromide, dimethyl sulfate, diethyl sulfate, di(cyclopropylmethyl)sulfate, methyl fluorosulfonate, trimethyloxonium fluoroborate, triethyloxonium fluoroborate, trimethyloxonium hexachloroantimonate, n-propyl or n-octyl trifluoromethane sulfonate, trimethyloxonium hexafluorophosphate, methyl trifluoromethane sulfonate, and allyl trifluoromethanesulfonate. Amongst the alkyl halides, while the chlorides and iodides may be used, the alkyl bromide is generally preferred as an alkylating agent. Relative to the corresponding alkyl bromides, under certain conditions, alkylations with alkyl chlorides tend to proceed slowly and alkyl iodides tend to lead to over alkylation of the tertiary alkaloid substrates. In one embodiment, therefore, the alkylating agent is methyl, ethyl, propyl, allyl, cyclopropyl, cyclopropylmethyl, or benzyl bromide. In a typical embodiment, the alkylating agent is methyl bromide or cyclopropylmethylbromide.

In general, an excess of alkylating agent will be employed for the reaction. The alkylating agent may be preformulated as a solution in an anhydrous solvent system (described below) prior to use. As an example, methyl bromide is cooled down to a temperature of about −10° C., and an aliquot is added into a vessel containing pre-cooled anhydrous 1-Methyl-2-Pyrrolidinone (NMP) also at a temperature of about −10° C. to form a stock solution of the alkylating agent, i.e., methyl bromide in NMP at −10° C. (MeBr/NMP). Large excesses (e.g., more than 3 equivalents of alkylating agent per equivalent of substrate), however, tend to lead to over-alkylation of the substrate. It is generally preferred, therefore, that the mole ratio of alkylating agent to substrate employed for the reaction be about 1:1 to 1.5:1, respectively. Further, the rate of addition of the alkylating agent to the reaction mixture can also have an effect upon the amount of undesired side-products with the amount of undesired side-products tending to increase as a function of increasing rates of addition. Thus, in some instances it may be preferred that the rate of addition be controlled to minimize this effect. For example, in certain embodiments, it is preferred that the rate of addition of alkylating agent be less than 0.02 equivalents of alkylating agent per minute per equivalent of tertiary N-substituted morphinan alkaloid substrate in the reaction mixture. In certain embodiments, it is preferred that the rate of addition be even slower; that is, in such embodiments it is preferred that the rate of addition be less than 0.01 equivalents of alkylating agent per minute per equivalent of tertiary N-substituted morphinan alkaloid substrate in the initial reaction mixture. In such embodiments, the rate of addition of alkylating agent will typically be between about 0.002 and 0.02 equivalents of alkylating agent per minute per equivalent of tertiary N-substituted morphinan alkaloid substrate in the reaction mixture. Thus, for example, if the reaction is carried out as a batch process, an initial reaction mixture is prepared comprising the quantity of tertiary N-substituted morphinan alkaloid substrate to be converted, and alkylating agent is introduced to the initial reaction mixture at a rate of less than 0.02 equivalents of alkylating agent per minute per equivalent of tertiary N-substituted morphinan alkaloid substrate in the initial reaction mixture over the period of addition of the alkylating agent. By way of further example, if the reaction is carried out as a continuous process (in which substrate and alkylating agent are continuously or semi-continuously introduced to the reaction mixture), alkylating agent is introduced to the reaction mixture at a rate of less than 0.02 equivalents of alkylating agent per minute per equivalent of tertiary N-substituted morphinan alkaloid substrate in the reaction mixture at the time of addition of the alkylating agent.

The reaction mixture in which the N-alkylation occurs contains a solvent system (that is, a solvent or mixture of solvents) and is anhydrous. In a preferred embodiment, the solvent system comprises an aprotic, dipolar solvent and is anhydrous. More specifically, the solvent system preferably comprises less than about 0.5 wt. % water, typically less than about 0.2 wt. % water, still more typically less than 0.1 wt. % water, and in some embodiments, less than 0.05 wt. % water. In addition, it is preferred that the aprotic, dipolar solvent (or mixture of aprotic dipolar solvents) constitute a significant fraction of the solvent system; for example, in one embodiment the aprotic, dipolar solvent(s) constitute(s) at least about 25 wt. % of the solvent system. For example, in some embodiments it is preferred that the aprotic, dipolar solvent(s) constitute(s) at least about 50 wt. % of the solvent system. In some embodiments, it is preferred that the aprotic, dipolar solvent(s) constitute(s) at least about 75 wt. % of the solvent system. In a further embodiment, the aprotic, dipolar solvent(s) constitute(s) at least about 90 wt. % of the solvent system. Exemplary aprotic dipolar solvents include dimethylacetamide, dimethylformamide, N-methylpyrrolidinone, acetonitrile, hexamethylphosphoramide ("HMPA"), and mixtures thereof. In one embodiment, the dipolar aprotic solvent is selected from the group consisting of dimethyl acetamide, dimethyl formamide, N-methylpyrrolidinone, HMPA and combinations thereof. Ni-methylpyrrolidinone (1-methyl-2-pyrrolidinone, NMP) is typically preferred, either alone or in combination with another aprotic, dipolar solvent.

The reaction may be carried out over a wide range of temperatures and pressures. In one embodiment, the reaction will be carried out at a temperature somewhere in the range of room temperature (about 25° C.) to about 90° C., typically about 55° C. to about 85° C. For example, the rate, conversion, yield and concentration of naltrexone base to the N-methylated product in anhydrous 1-methyl-2-pyrrolidinone is advantageously and dramatically increased at lower reaction temperatures (<70° C.) as compared to the reaction in acetone carried out at 125° C. to 140° C. (>10 atm) over 24 hours.

The N-alkylation reaction may be carried out over a range of pressures. For example, when the alkylating agent is methyl bromide and the methyl bromide gas (MeBr) is dissolved in anhydrous 1-methyl-2-pyrrolidinone (NMP), the gas is predominantly retained at temperatures of as high as 85° C. at relatively modest elevated pressures (e.g., ≤2 atmospheres) without the need for expensive pressure vessels. In one embodiment, therefore, the N-alkylation reaction is carried out at a pressure not in excess of 1.5 atmospheres in an aprotic dipolar solvent such as NMP, or in a solvent mixture comprising NMP. Advantageously, for example, the N-alkylation reaction may be carried out at a pressure of 1 to 1.25 atmospheres or even at atmospheric pressure.

In accordance with one aspect of the present invention, it has been determined that addition of an acid to the reaction mixture tends to suppress ionization of the phenolic C(3) hydroxy group of a tertiary N-substituted morphinan alkaloid having a C(3) hydroxy substituent. The acid is preferably an anhydrous acid. In addition, it is preferably a strong mineral or organic acid. For example, the acid may be a carboxylic acid, a phosphonic acid, a sulfonic acid or a mixture thereof. Alternatively, a small amount of a preformed alkaloid acid salt may be added to its alkaloid base in order to suppress ionization of the alkaloid base; for example, naltrexone hydrobromide may be added to naltrexone base. By way of further example, the acid may be HBr, HCl, $H_2SO_4$, $NaHSO_4$, $NaH_2PO_4$, or $Na_2HPO_4$, containing less than about 0.5 wt. % water, less than 0.2 wt. % water, less than 0.1 wt. % water, or even less than 0.05 wt. % water. In one embodiment, for example, it is preferred that the acid be HBr gas, or HCl gas, particularly HBr gas. Conversion rates tend to decrease with increasing acid concentrations. Thus, it is generally preferred that the amount of acid included in the reaction mixture be initially less than 0.25 equivalents of acid per equivalent of substrate. In certain embodiments, it is preferred that the amount of acid included in the reaction mixture be about 0.1 equivalents of acid per equivalent of substrate. In some embodiments, it may be preferred that even less acid be employed; for example, in some embodiments it is preferred that the amount of acid be less than 0.10 equivalents of acid per equivalent of substrate, less than 0.05 equivalents of acid per equivalent of substrate, or even less than 0.01 equivalents of acid per equivalent of substrate. In a typical reaction, a stock solution of a strong, anhydrous acid is prepared in the anhydrous solvent and added in aliquots. For example, in a reaction in which HBr is the strong anhydrous acid, a sample withdrawn from a source of hydrogen bromide (HBr) cooled to a temperature of about −70° C. is added to a sample of 1-methyl-2-pyrrolidinone (N-methylpyrrolidone; NMP) at a temperature of about −20° C. and the solution allowed to warm to room temperature. The solution may then be further diluted with NMP to form a stock solution of HBr in NMP (HBr/NMP) at a desired concentration.

Typically, the substrate for the N-alkylation reactions described herein (e.g., involving substrates containing a C(3) hydroxide) is a dehydrated base. For example, in reactions utilizing naltrexone, the anhydrous base may be prepared from naltrexone hydrochloride which has been dried under vacuum until the water content is reduced to about 2% or less by Karl-Fischer analysis. A hydrated base (e.g., naltrexone dihydrate, Naltrexone.$2H_2O$) may be used in alkylations that involve prior protection of the phenolic C(3) hydroxide. Further, it has been observed advantageously that the presence of a strong acid (such as HBr) in the reaction system permits use of partially hydrated naltrexone (Naltrexone.$2H_2O$) as a starting material instead of anhydrous naltrexone. Therefore, acidification of the reaction medium affords reduction in processing costs by eliminating the costs associated with dehydration of naltrexone base prior to alkylation.

In general, relatively concentrated solutions of the substrate are preferred. That is, the initial reaction mixture preferably comprises no more than about 2 equivalents of solvent for each equivalent of N-substituted morphinan alkaloid substrate. In some embodiments, the initial reaction mixture comprises no more than about 1.75 equivalents of solvent for each equivalent of N-substituted morphinan alkaloid substrate. In other embodiments, the initial reaction mixture comprises no more than about 1.5 equivalents of solvent for each equivalent of N-substituted morphinan alkaloid substrate.

In general, the quaternary derivative resulting from the N-alkylation is more ionic than the N-substituted morphinan alkaloid substrate. As a result, the quaternary derivative tends to have less solubility in non-polar solvents than the N-substituted morphinan alkaloid substrate. To aid in recovery of the quaternary derivative from the reaction mixture, a solvent (or mixture of solvents) less polar than the aprotic, dipolar solvent(s) may be introduced to the reaction mixture to cause the quaternary derivative to precipitate from solution while leaving the unreacted N-substituted morphinan alkaloid substrate in solution. Such solvents, sometimes referred to as non-solubilizing solvents (for the quaternary derivative) are preferably employed in one embodiment of the present invention. Typically, the non-solubilizing solvent(s) is(are) introduced to the reaction mixture upon completion of the N-alkylation reaction to cause the quaternary derivative to precipitate from the reaction mixture. Alternatively, however, a fraction of the non-solubilizing solvent(s) may be added to the reaction mixture prior to, at the initiation of, or during the course of the N-alkylation reaction. In this alternative however, the kinetics of the alkylation may be adversely affected. Preferably, the quaternary derivative has a solubility of less than 5 wt. % in the non-solubilizing solvent at 1 atmosphere and 25° C. In addition, the non-solubilizing solvent is preferably more miscible with 1-methyl-2-pyrrolidinone than with water; for example, the non-solubilizing solvent preferably has a solubility of less than about 30 wt. % in water at 1 atmosphere and 25° C. Exemplary non-solubilizing solvents include chloroform, dichloromethane, ethyl acetate, propyl acetate, methyl ethyl ketone, methyl butyl ketone, ether, hydrocarbon, toluene, benzene, chlorobenzene, bromobenzene and mixtures thereof. Of these, chloroform is sometimes preferred.

In general and regardless of synthetic route, N-alkylations of morphinan substrates that contain a C(3) hydroxy moiety may yield undesirable C(3) alkoxy morphinans. Crude product mixtures containing C(3) hydroxy and C(3) alkoxy morphinans may be purified by adding strong base, e.g., sodium methoxide, NaOH or KOH in methanol/water, heating the mixture to convert the C(3) hydroxy morphinan to its oxide salt (e.g., sodium salt), adding additional methanol, cooling to precipitate the salt, filtering and drying. Advantageously, the C(3) alkoxy morphinan remains in solution and does not precipitate along with the salt; as a result, the salt and the C(3) alkoxy morphinan may be readily separated.

The desired N-alkyl morphinan may be regenerated from the salt by redissolving the salt (for example, in a methanol/water solution), adjusting the solution to a low pH (for example, a pH of 0.5 to 1 using 45% hydrobromic acid) to regenerate a hydroxy group at the C(3) position, and precipitating the product. In a preferred embodiment, the precipitated product is recovered by vacuum filtration, washing with additional methanol and drying to 75° C.

In one embodiment, two or more of the aforementioned preferred steps or features are combined. For example, in one preferred embodiment, the average rate of addition of the alkylating agent is controlled (as previously described) to minimize over-alkylation of the substrate. By way of further example, in one embodiment the average rate of addition of the alkylating agent is controlled (as previously described) to minimize over-alkylation of the substrate and a non-solubilizing solvent for the quaternary derivative is added to the reaction mixture to cause the quaternary derivative to precipitate from the reaction mixture while the substrate substantially remains dissolved in the solvent system. By way of further example, in one embodiment the average rate of addition of the alkylating agent is controlled (as previously described) to minimize over-alkylation of the substrate and a strong anhydrous acid (in the amounts previously described) is included in the reaction mixture to inhibit alkylation of the C(3) hydroxy substituent of a tertiary N-substituted morphinan alkaloid substrate. By way of further example, in one embodiment the average rate of addition of the alkylating agent is controlled (as previously described) to minimize over-alkylation of the substrate, a strong anhydrous acid (in the amounts previously described) is included in the reaction mixture to inhibit alkylation of the C(3) hydroxy substituent of a tertiary N-substituted morphinan alkaloid substrate, and a non-solubilizing solvent for the quaternary derivative is added to the reaction mixture to cause the quaternary derivative to precipitate from the reaction mixture while the substrate substantially remains dissolved in the solvent system. In one preferred embodiment, in each of these aforementioned combinations, methyl bromide is used as the alkylating agent, the pressure of the reaction mixture is less than 2 atmospheres (preferably 1 to 1.5 atmospheres), and the temperature of the reaction mixture is not in excess of 80° C.

In one preferred embodiment the N-alkylation reaction is carried out at a pressure of less than 1.25 atmospheres, the aprotic dipolar solvent constitutes at least 75 wt. % of the solvent system, and the aprotic dipolar solvent is 1-methyl-2-pyrrolidinone. In addition, in this preferred embodiment the anhydrous solvent system contains less than 0.2 wt. % water, preferably less than 0.1 wt. % water, more preferably less than 0.05 wt. % water, and said anhydrous system is maintained in a moisture-free atmosphere in a reaction vessel. The substrate in this preferred embodiment corresponds to Formula 1 wherein Y and Z are independently —OCH$_3$, —OAc, —OTHP, —OSiR$_3$, —OBn, —OBz, —OBs, —OTs, or —OMs wherein each R is independently hydrocarbyl. In one particularly preferred embodiment, the substrate is naltrexone ((5α)-17-(cyclopropylmethyl)-4,5-epoxy-3,14-dihydroxymorphinan-6-one), oxymorphone ((5α)-4,5-epoxy-3,14-dihydroxy-17-methylmorphinan-6-one), oxycodone ((5α)-4,5-epoxy-14-hydroxy-3-methoxy-17-methylmorphinan-6-one), hydromorphone ((5α)-4,5-epoxy-3-hydroxy-17-methylmorphinan-6-one), naloxone ((5α)-4,5-epoxy-3,14-dihydroxy-17-(2-propenyl)morphinan-6-one), nalmefene ((5α)-17-(cyclopropylmethyl)-4,5-epoxy-6-methylenemorphinan-3,14-diol) or nalbuphine ((5α)-17-(cyclobutylmethyl)-4,5-epoxymorphinan-3,6,14-triol). Alternatively, the substrate in this preferred embodiment corresponds to Formula 3 and the substrate is, for example, morphine ((5α,6α)-7,8-didehydro-4,5-epoxi-17-methylmorphinan-3,6-diol), codeine ((5α,6α)-7,8-didehydro-4,5-epoxi-3-methoxy-17-methylmorphinan-6-ol), codeinone ((5α)-7,8-didehydro-4,5-epoxy-3-methoxy-17-methylmorphinan-6-one) or 14-hydroxy-codeinone ((5α)-7,8-didehydro-4,5-epoxy-14-hydroxy-3-methoxy-17-methylmorphinan-6-one).

Alternate Embodiment for N-alkylation of C(3)-Hydroxy Morphinan Alkaloids

N-alkylation of a C(3)-hydroxy morphinan alkaloid substrate (Formula 11) can produce undesired C(3)-alkoxy morphinan side products because of a parallel alkylation of the unprotected C(3)-hydroxy group. This process is exemplified in Scheme 1 below where the undesired side products are C(3)-methoxy morphinan (Formula 11B) and N-alkylated C(3)-methoxy morphinan (Formula 11C) resulting from O-alkylation of the phenolic C(3)-OH, wherein R$^1$, R$^2$, A, X, and Y are as defined in connection with Formulae 1 and 1A.

SCHEME 1.

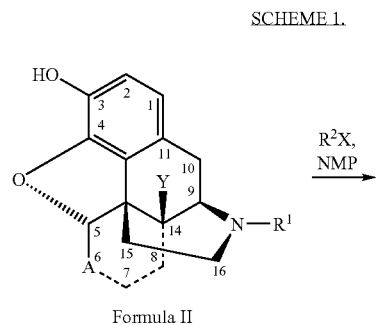

Formula II

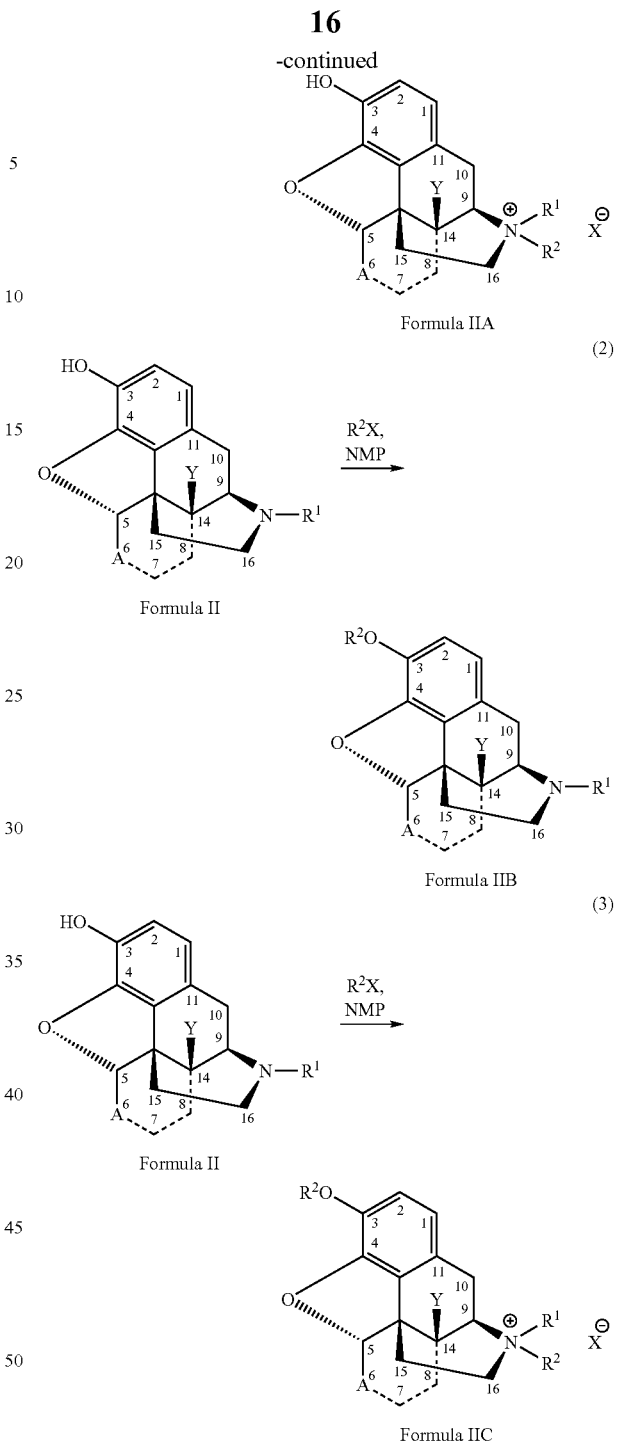

To inhibit the side reaction (i.e., C(3)-O-alkylation), the phenolic group (C(3)-OH) of the tertiary morphinan alkaloid may first be protected to generate the C(3)-OH-protected tertiary morphinan alkaloid. A single protection reaction may be carried out, or a series of protecting reactions may be carried out in order to affect more complete conversion of the C(3)-O-protected derivative from the C(3)-hydroxy morphinan starting material. In one embodiment, a single protection step is carried out to convert the C(3)-hydroxy morphinan starting material to the C(3)-protected hydroxy derivative. In another embodiment, two protection steps are carried out to convert the C(3)-hydroxy morphinan starting material to the C(3)-protected hydroxy derivative. In another embodiment, three protection steps are carried out to convert the C(3)-hydroxy morphinan starting material to the C(3)-protected hydroxy derivative. In another embodiment, three or more protection steps are carried out to convert the C(3)-hydroxy morphinan starting material to the C(3)-protected hydroxy derivative. Regardless of the number of protection reactions employed, the protected substrate is then N-alkylated to yield a protected quaternary morphinan alkaloid. The protecting group is subsequently removed to yield the desired quaternary morphinan alkaloid salt.

Accordingly, in certain embodiments, the tertiary morphinan alkaloid base possesses a protected C(3)-OH wherein the tertiary N-substituted morphinan alkaloid substrate has the structure of Formula 111 and the quaternary derivative has the structure of Formula 111A:

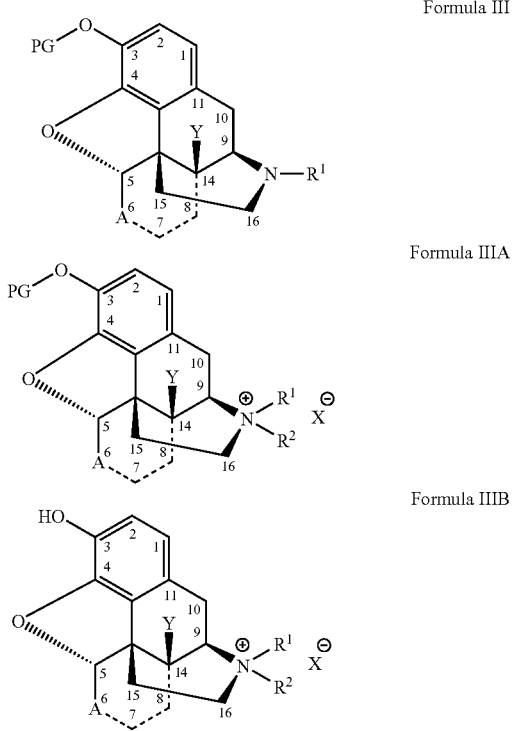

Formula III

Formula IIIA

Formula IIIB wherein A, $A_1$, $R^1$, $R^2$, $X^1$, and Y are as defined in connection with Formulae 1 and 1A; and wherein PG is a hydroxy protecting group. In these embodiments, a compound of Formula 111B is produced upon removal of the hydroxy protecting group.

Representative hydroxy protecting groups include optionally substituted hydrocarbyl, $C_1$-$C_6$-alkyl, $C_2$-$C_{10}$-alkyloxy-alkoxy; $C_2$-$C_6$-alkenyl; $C_2$-$C_6$-alkynyl; saturated cyclic $C_3$-$C_6$-alkyl; $C_4$-$C_{16}$-(cyclical saturated)alkenyl; $C_4$-$C_{16}$-(cyclical saturated)alkynyl; $C_7$-$C_{16}$-arylalkyl; $C_8$-$C_{16}$-arylalkenyl; $C_8$-$C_6$-arylalkynyl; $C_2$-$C_6$-alkanoyl; $C_3$-$C_6$-alkenoyl; $C_3$-$C_6$-alkynoyl; $C_8$-$C_{16}$-arylalkanoyl; $C_9$-$C_{16}$-arylalkenoyl; $C_9$-$C_{16}$-arylalkynoyl; sulfonyl or phosphonyl.

A range of hydroxy protecting groups which may be used comprise ethers (alkoxy) and esters (acyloxy); (see T. W. Greene and P. G. M. Wuts, Protective Groups in Organic Synthesis (3rd edition), J. Wiley & Sons In., NY 1999, chapter 3). Common ether protective groups comprise methyl, methoxymethyl, propargyl, benzyl, trityl, silyl, tris-($C_1$-$C_6$-alkyl)silyl or tris-($C_7$-$C_{16}$-arylalkyl)silyl. Common ester protective groups comprise, formate, acetate, alkyl carbonate, aryl carbonate, aryl carbamate alkylsulfonate, arylsulfonate, triflate, phosphonate or phoshinates. Exemplary hydroxy protecting groups include methoxymethyl, 1-ethoxyethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

Introduction of a protective group such as benzyl, trityl or silyl to the C(3)-hydroxy group is achieved by C(3)-O-benzylation, C(3)-O-tritylation or C(3)-O-silylation of the morphinan compounds using benzyl halogenides, trityl halogenides, or trialkyl halogen silanes. Such derivatization is effected in a solvent such as toluene, chloroform, chloromethane, chlorobenzene, acetone, dimethyl formamide, or combinations thereof, and in the presence of a base comprising sodium bicarbonate, potassium carbonate, triethylamine, sodium hydroxide, potassium bicarbonate, or pyridine. Alternately, ester protective groups may be introduced in the form of the corresponding acyl halide or anhydride in aqueous media or in dimethyl formamide in the presence of a base such as sodium bicarbonate, sodium hydroxide, potassium carbonate, potassium bicarbonate, pyridine or triethylamine. Further still, the hydroxy protection reaction may be carried out in aqueous-organic solvent mixtures being combinations of the above listed solvents in the presence of a base listed above. In one particular embodiment, the protective group is an acyl moiety, such as an acetyl group, introduced by treatment of the C(3)-hydroxy morphinan with an acyl protecting group precursor. Following the hydroxy protection step and the optional washing/filtration/solvent exchange steps discussed below, the protected morphinan is then quaternized (see Scheme 1).

The C(3)-hydroxy morphinan may be in the free base or salt form; typically, however, the C(3)-hydroxy morphinan is in the free base form. In either case, the morphinan is preferably combined with water and a base (e.g., sodium hydroxide) to assist in the formation of a substantially homogeneous reaction mixture (e.g., to solubilize the compound). Typically, the C(3)-hydroxy morphinan starting material is combined with the water in the reaction vessel prior to the addition of the base. Alternatively, however, the water and the base may be combined and thereafter added to the reaction vessel containing the C(3)-hydroxy morphinan starting material. It will be understood that where C(3)-hydroxy morphinan salt forms are employed, the amount of water and base to solubilize the morphinan may vary. For instance, where the C(3)-hydroxy morphinan salt is the hydrochloric acid salt two or more equivalents of the base may be necessary to completely solubilize the compound.

After solubilization, the solubilized compound is combined with a water immiscible solvent, resulting in the formation of a biphasic solvent system; the organic layer of the biphasic mixture includes the water immiscible solvent (and any water that combined with the solvent in the form of an emulsion), and the aqueous layer of the biphasic mixture includes the C(3)-hydroxy morphinan starting material and water. Exemplary water immiscible solvents that may be used include, but are not limited to, chlorobenzene, chloroform, dichloromethane, 1,2-dichloroethane, diethyl ether, ethyl acetate, propyl acetate, tetrahydrofuran, toluene, xylene, combinations thereof, and the like. In a particular embodiment, the water immiscible solvent is toluene.

In order to affect C(3)-protection of the C(3) hydroxy group, the layers of the biphasic mixture are treated with a protecting group precursor. The protecting group precursor will generally vary depending on the particular protecting group that is desired for the C(3)-hydroxy position (as described above). In one embodiment, the protecting group is an acyl protecting group; more preferably an acetyl protecting group. According to this preferred embodiment, for example, the protecting group precursor is typically acetic anhydride. While the discussion herein may focus on the use of acetic anhydride as the protecting group precursor in a multi-stage protection protocol, it will be understood that other protecting group precursors may be used to introduce a protecting group to the C(3)-hydroxy position with minor modifications to conditions that are within the ambit of one of skill in the art.

In a typical C(3)-hydroxy protection reaction involving the introduction of an acetyl group at the C(3)-hydroxy position, for example, the treatment of the biphasic mixture with acetic anhydride causes the C(3)-protected hydroxy derivative of the C(3)-hydroxy morphinan starting material to precipitate out of the aqueous phase and dissolve into the organic phase of the biphasic mixture. Thereafter, the organic layer includes the C(3)-protected hydroxy derivative (the predominant, but not exclusive, morphinan species in the solvent layer), the water immiscible solvent, and typically a small quantity of the unreacted C(3)-hydroxy morphinan starting material, and the aqueous layer includes any unreacted or excess protecting group precursors a majority of the unreacted C(3)-hydroxy morphinan starting material, and water.

In the initial (i.e., first) protection reaction, an excess of the protecting group precursor (e.g., acetic anhydride) is generally preferred. In the second, third, and further protection reactions, lesser amounts of protecting group precursor may be employed, as smaller quantities of C(3)-hydroxy morphinan typically remain. As a result of excess acetic anhydride in an initial protection reaction, the pH of the biphasic reaction mixture tends to decrease as a result of the formation of acetic acid which may hydrolyze the C(3)-protected hydroxy derivative and/or extract the protected derivative from the organic layer into the aqueous layer. Thus, after treatment with the protecting group precursor, the pH of the reaction product mixture may be optionally adjusted to a more basic pH; for example, to a pH of about 9.5 to about 10.5, more preferably 10.0, with a base such as sodium hydroxide or potassium hydroxide. In general, adjusting the pH of the protection reaction mixture can improve downstream yields of the desired products. Thus, in certain embodiments, the pH of the protection reaction mixture is preferably adjusted (i.e., to a more basic pH) after the protection reaction and prior to the next process step.

The pH adjustment step, if performed, may cause an undesirable hydrolysis (i.e., removal) of the C(3)-hydroxy protecting group. Additionally or alternatively, unreacted (i.e., unprotected) C(3)-hydroxy tertiary N-unsubstituted morphinan alkaloid may still be present in the reaction mixture. Thus, as noted above, it may be desirable to perform a second C(3)-hydroxy protection reaction, a third C(3)-hydroxy protection reaction, or more. For example, the protection reaction may be carried out once, twice, three times, or more, in order to protect the C(3)-hydroxy group of any unreacted or hydrolyzed C(3)-hydroxy tertiary N-unsubstituted morphinan alkaloid that remains after the initial (or subsequent) protection reactions and/or pH adjustment steps. In one embodiment, the C(3)-hydroxy protection reaction is repeated at least once. In another embodiment, the C(3)-hydroxy protection reaction is repeated twice; according to this embodiment, for example, the C(3)-O-protected tertiary morphinan alkaloid substrate is formed after a first protection reaction, and additional quantities of the C(3)-O-protected tertiary morphinan alkaloid substrate are formed after a second and third protection reaction.

Each successive protection reaction may be carried out in substantially the same manner as the previous protection reaction, and may or may not be followed by a pH adjustment step as described above. Additionally or alternatively, minor modifications in the protection reaction may be made. For instance, in one embodiment, the first protection reaction generally involves treating the reaction mixture containing C(3)-hydroxy tertiary N-unsubstituted morphinan alkaloid with a protecting group precursor (e.g., acetic anhydride or other precursor capable of protecting the C(3)-hydroxy group with a acyl or acetyl moiety), and subsequently adjusting the pH of the reaction mixture to about 9.5 to about 10.5. While additional protection reactions may be carried out in a similar manner, smaller quantities of the protecting group precursor are generally employed in the subsequent (i.e., second and third) protection reactions since lesser quantities of unprotected C(3)-hydroxy morphinan alkaloid are generally present.

Where at least two protection reactions are performed, the resulting C(3)-protected product mixture may be optionally filtered to remove any sediment or other insoluble components or byproducts from the mixture. In general, conventional filtration techniques may be employed (e.g., macro- or micro-filtration). In the embodiments in which three protection reactions, or more, are employed, the filtration step is preferably carried out after the second protection reaction.

After the first one or two protection steps have been performed and the resulting mixture is optionally filtered, the biphasic reaction product mixture may be subjected to an aqueous/organic extraction to remove by-products and other impurities. In general, conventional aqueous/organic extraction techniques may be utilized. In a particular embodiment, additional water immiscible solvent (e.g., toluene) is added to the biphasic mixture containing the C(3)-protected hydroxy derivative in the organic layer. Regardless of whether additional solvent is added to the biphasic mixture, the organic layer containing the desired C(3)-protected hydroxy derivative is extracted and separated from the aqueous layer containing the by-products and impurities, and the aqueous layer is discarded. The aqueous/organic extraction may be repeated as desired, and the organic layers collected and combined.

In order to remove unreacted, excess, or residual protecting group precursor and/or undesirable salts of the morphinan alkaloid (e.g., formed by reaction with the protecting group precursor) from the reaction mixture prior to solvent exchange and quaternization (described in detail herein), the combined organic layer fractions are preferably washed with a buffer solution. Typically, the separated organic mixture including the C(3)-protected hydroxy derivative is buffered to a pH of about 8.5 to about 9.5 with the buffer solution. In a particular embodiment, the pH of the organic layer is buffered after the protection reaction(s) to a pH of about 9.0. In general, a variety of pH buffers may be employed, provided the buffer solution(s) is/are capable of buffering the reaction product mixture to a pH within the desired pH range and/or the buffer solutions do not otherwise affect the morphinan alkaloid backbone and the substituents thereon. Suitable buffer solutions include, for example, those comprising a borate buffer (e.g., tetraborate), a carbonate buffer, a phosphate buffer, a tertiary amine buffer (e.g., triethanolamine and tris(hydroxymethyl)aminomethane), and combinations thereof. In a particular embodiment, the buffer solution comprises a phosphate buffer. In another particular embodiment, the buffer solution is a phosphate buffer. In order to remove a substantial portion of the protecting group precursor, reaction times for the buffer wash can range anywhere from several minutes to several hours depending on the particular reagents utilized. Typically, the organic phase containing the C(3)-protected hydroxy derivative is treated with the buffer solution for about 30 minutes to about 90 minutes; preferably about 60 minutes.

Because the C(3)-O-protecting group may be undesirably removed (i.e., deprotected) in the presence of water, relatively anhydrous conditions are generally preferable for both the protection reaction(s) and the subsequent quaternization. Thus, the organic layer is preferably subjected to drying step to reduce the water content of the organic layer. A variety of drying techniques may be employed in this stage including, for example, distillation, molecular sieves, anhydrous salts, and Dean-Stark traps, for example, are generally effective, among other conventional drying methods. Where a water scavenger is employed, for example, a variety of water scavengers may be utilized, provided that the presence of the water scavenger does not adversely affect the quaternization reaction or the morphinan alkaloid backbone and the substituents thereon (e.g., by deprotection of the C(3)-hydroxy group). Suitable water scavengers include, but are not limited to, compounds corresponding to the formula: $R_YC(OR_Z)_3$, wherein $R_Y$ is hydrogen or hydrocarbyl and $R_Z$ is hydrocarbyl. Preferably, $R_Y$ is hydrogen or alkyl and $R_Z$ is alkyl; in this embodiment, for example, the water scavenger may correspond to trimethoxymethane, trimethoxyethane, trimethoxypropane, trimethoxybutane, trimethoxypentane, triethyoxyethane, triethoxypropane, combinations thereof and the like. Alternatively, the water scavenger may be a desiccant such as anhydrous inorganic salts that can form hydrates, e.g., magnesium sulfate ($MgSO_4$) or sodium sulfate ($Na_2SO_4$). Desiccants, however, are generally less preferred due to their tendency to form a suspension in the reaction mixture.

In one embodiment, the water content of the organic layer is reduced by distillation to remove any water present in the organic layer (e.g., through formation of an emulsion with the water immiscible solvent). According to this technique, the water removal can be observed, and once a substantial portion is withdrawn from the system the resulting dewatered organic layer is preferably further treated with additional protecting group precursor (e.g., acetic anhydride) to provide more complete conversion of the C(3)-hydroxy morphinan to the C(3)-protected derivative. As noted above with additional protection reactions, this further protection reaction may require less acetic anhydride (or other protecting group precursor) as compared to the first or second protection reaction, since there will typically be less unprotected C(3)-hydroxy morphinan present in the organic layer.

After the C(3)-hydroxy protection steps and optional washing and filtration steps discussed above, the C(3)-O-protected morphinan may be quaternized. Typically, methyl bromide is the preferred agent for methylating C(3)-OH-protected tertiary morphinan alkaloids and the quaternization is carried out in NMP as previously described. It has been discovered, however, that dimethyl sulfate can also be employed as the methylating agent for the C(3)-hydroxy protected substrate with high yields of the quaternized product. The alkylation using dimethyl sulfate is preferably carried out in toluene in the presence of sodium carbonate, however, other bases ($NaHCO_3$, $K_2HPO_4$, i-$Pr_2Net$, 2,6-lutidine, and 1,8-bis(dimethylamino)naphthalene), also afford the desired product, albeit typically in lower yields.

In one embodiment, the hydroxy protecting group is the acetate group when the alkaloid substrate is naltrexone and a typical sequence of reactions is shown in Scheme 2 below, wherein $R^2$ and X are as defined in connection with Formulae 1 and 1A.

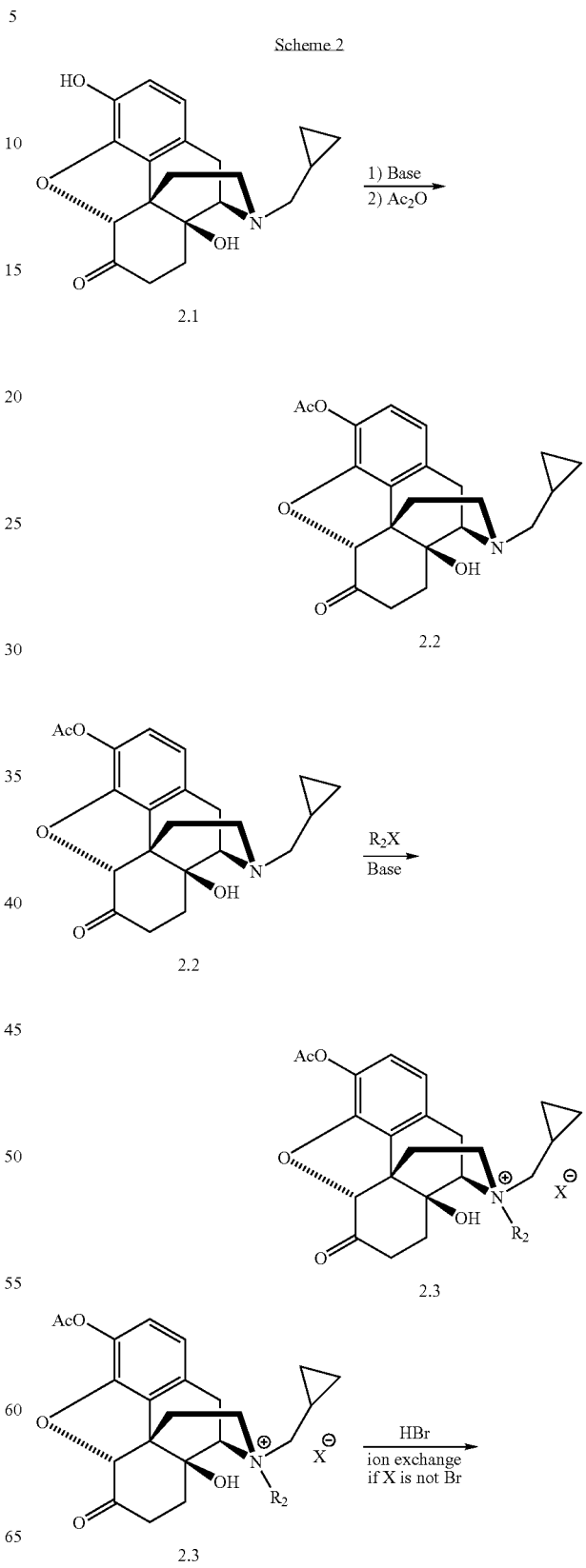

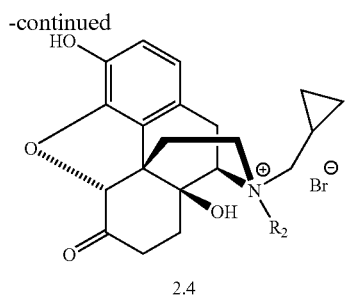

2.4

In this embodiment, the C(3)-OH protection is effected in a basic medium comprising i-Pr$_2$NEt, 2,6-Lutidine, or aqueous solutions of NaOH, NaHCO$_3$, Na$_2$CO$_3$, or K$_2$HPO$_4$. Further, in this embodiment, the alkylating agent (i.e., R$_2$X) comprises a methyl, ethyl, propyl, allyl, cyclopropyl, propargyl or benzyl salt of an anion such as a halide, sulfate, sulfonate, fluorosulfonate, methylsulfate, ethylsulfate, trifluoromethane-sulfonate, hexachloroantimonate, hexafluorophosphate, or tetrafluoroborate. Representative examples include methyl bromide, dimethyl sulfate, diethyl sulfate, methyl fluorosulfonate, trimethyloxonium fluoroborate, triethyloxonium fluoroborate, trimethyloxonium hexachloroantimonate, n-propyl or n-octyl trifluoromethane sulfonate, trimethyloxonium hexafluorophosphate, methyl trifluoromethane sulfonate, and allyl trifluoromethane-sulfonate. Typically, the alkylating agent is an alkyl halide or sulfate. Preferably, the alkylating agent is MeBr. Alternatively, oxymorphone may be substituted for naltrexone and a cyclopropylmethyl alkylating agent may be substituted for the methylating agent in Reaction Scheme 2 to yield S-methylnaltrexone.

The quaternization of the C(3)-OH-protected alkaloid morphinan substrate is typically carried out at a low pressure (≤2 atm) in the temperature range of from about 60 to about 105° C. Preferably, the reaction is carried out within a temperature range of about 60 to 85° C. Typically, the reaction lasts for a duration of about 6 h-24 h; preferably the duration is for about 16 h-22 h. In a preferred embodiment, N-alkylation of the C(3)-OH-protected alkaloid morphinan substrate is carried out with MeBr in NMP; at about 60-85° C.; for a duration of between 16 h-22 h. Typically, modest pressure differentials of about 4 psi are realized upon addition of MeBr. Upon completion of the quaternization reaction, the naltrexone methobromide is generated by acid hydrolysis to remove the C(3)-O-protecting group and precipitation from alcohol.

In order to provide the C(3)-O-protected morphinan in the desired solvent for the quaternization (e.g., NMP), certain embodiments employ solvent exchange techniques on the reaction product mixture resulting from the single or multiple protection reaction(s) (i.e., the organic phase containing the C(3)-protected hydroxy derivative). Generally, in the solvent exchange, the first solvent preferred in the protection reactions (e.g., the water immiscible solvent) is removed and replaced with a second solvent preferred in the quaternization reaction (e.g., NMP). Thus, the solvent exchange is accomplished by concentrating the protection reaction mixture, thus forming a concentrate including the C(3)-protected hydroxy derivative, and adding the second solvent preferred for the quaternization reaction to the concentrate. In a preferred embodiment, the concentrate is formed by distilling the organic phase to remove all, substantially all, or part of the organic solvent, leaving a concentrate or oil including the C(3)-protected hydroxy derivative. To affect the solvent exchange by distillation, for example, the organic phase may be heated to the boiling point of the protection reaction solvent (i.e., the water immiscible solvent) to distill (either atmospheric or reduced pressure) such solvent from the reaction product. Similarly, if the water immiscible solvent for the protection reaction forms an azeotrope with water, then part or all of the organic solvent with water may be removed by distillation of the azeotrope. Other methods of concentrating the organic layer, however, may be employed and will be apparent to one of skill in the art.

After concentration of the C(3)-protected hydroxy derivative and removal of the water immiscible solvent and other undesirable substances in the reaction mixture (e.g., water, excess or unreacted protecting group precursor, by-products, etc.) is accomplished (e.g., by distillation), the C(3)-O-protected morphinan generally remains in the form of concentrate. Where all or substantially all of the organic solvent has been removed, the concentrate may be in the form an oil including the C(3)-O-protected morphinan. In the instances where the preferred alkylating agent cannot be effectively added to the concentrate in a manner that will result in quaternization, the concentrate may be dissolved in the preferred solvent for the quaternization reaction (i.e., dissolution of the concentrate or oil in the solvent). Suitable solvents for the quaternization reaction are described elsewhere herein, and include NMP and dimethyl sulfate. Preferably, the dissolution solvent is an anhydrous solvent system as described above. In a particular embodiment, additional protecting group precursor may be added to the concentrate in addition to the second (quaternization) solvent in an effort to further provide C(3)-O-protected morphinan substrate material (i.e., in a second, third, etc., protection reaction).

In an embodiment, hydrolysis of the C(3)-O-protected quaternized product is effected in aqueous HBr. Approximately 0.5 to about 1.5 equivalents of HBr is typically employed (based on C(3)-acetoxy naltrexone); preferably the ratio of HBr to C(3)-acetoxy naltrexone is about 1:1. The acidic mixture is stirred at about 60-65° C. for approximately 30-60 minutes for removal of residual MeBr, then heated to about 75-85° C., and stirred until hydrolysis of C(3)-acetoxy naltrexone methobromide is complete as monitored by periodic HPLC analysis of samples. Typically, the hydrolysis is complete within 5 hours.

Upon removal of the C(3)-hydroxy group by way of hydrolysis as described above, any residual or unreacted alkylating agent present in the reaction mixture may result in undesirable C(3)-O-alkylation of the C(3)-hydroxy group. For instance, methyl bromide alkylating agent can cause the undesirable formation of a C(3)-O-methyl morphinan quaternary product. Thus, it is generally preferable to quench the quaternization reaction and purge the alkylating agent from the system. This can be accomplished, for example, by introducing a purge agent into the reaction mixture/vessel following quaternization and prior to hydrolysis. A variety of quench/purge agents may be employed, and the choice of a particular purge agent may depend on the particular alkylating agent selected and/or the various other process conditions. For instance, where methyl bromide is used as the alkylating agent, the purge agent preferably comprises a bromide-containing agent to assist in the removal (purge) of the methyl bromide from the system.

In a particular embodiment in which methyl bromide is employed in the quaternization reaction, the purge agent introduced to the system after quaternization is hydrogen bromide or a salt thereof (e.g., a trialkylammonium hydrobromide such as triethylammonium hydrobromide). The bromide-containing purge agent is generally introduced in the presence of a solvent. The solvent for the purge agent is generally one which is compatible with hydrogen bromide (or salts thereof) and which will not adversely affect the quaternary morphinan. Suitable solvents include various carboxylic acids such as acetic acid; aprotic, non-nucleophilic solvents (e.g., NMP); esters (such as, for example, methyl acetate, ethyl acetate, propyl acetate, isopropyl acetate, butyl acetate, isobutyl acetate, and ethyl formate); and combinations thereof. The concentration of bromide in the purge agent is not narrowly critical; generally only a catalytic amount of bromide is necessary to affect the desired removal of methyl bromide from the reaction vessel. Thus, the concentration of hydrogen bromide (or salt thereof) in the solvent can vary from less than 1% (w/w) to nearly 100% (w/w); in a preferred embodiment, the purge agent comprises 33% hydrogen bromide or salt thereof in acetic acid.

The product of the acid hydrolysis of the quaternized C(3)-hydroxy-protected alkaloid morphinan is precipitated by addition of alcohol to the cooled acidic solution under a nitrogen atmosphere. In the embodiment described above, the mixture is cooled to about 50-55° C. and an optimal amount of methanol (1.0 wt. equiv based on the initial NMP) is added for precipitation of naltrexone methobromide. Finally, the mixture is cooled to room temperature and then stirred for about 1 hour at approximately 0-5° C. for complete precipitation of the product (monitored by HPLC analysis). The product is then filtered, washed with cold methanol (about 1-2 mL/g C(3)-acetoxy naltrexone), and isolated as a wet cake. The product is optimally recrystallized utilizing optimized conditions (about 1.5-2.0 mL water/g naltrexone methobromide, about 3.0-4.0 mL methanol/g naltrexone methobromide, and about 12-24 mole % HBr based on naltrexone methobromide) to afford purified naltrexone methobromide in high yields and purity.

The protection, quaternization, purge, and hydrolysis steps may be carried out in the order as described, and/or various extraction/separation and wash steps may be interdispersed between these various stages as described above.

In one embodiment, the process of the invention comprises (a) a first protection step, (b) a solvent extraction/separation step, (c) a drying step, (d) a second protection step, (e) a concentration step, (f) a dissolving step, (g) a quaternization step, and (h) a deprotection step, whereby each of steps (a)-(h) are substantially as described above. In another embodiment, the process of the invention comprises (a) a first protection step, (b) a solvent extraction/separation step, (c) a second protection step, (d) a concentration step, (e) a dissolving step, (f) a quaternization step, and (g) a deprotection step, whereby each of steps (a)-(g) are substantially as described above. In another embodiment, the process of the invention comprises (a) a first protection step, (b) a pH adjustment step, (c) a solvent extraction/separation step, (d) a drying step, (e) a second protection step, (f) a concentration step, (g) a dissolving step, (h) a quaternization step, and (i) a deprotection step, whereby each of steps (a)-(i) are substantially as described above. According to each of these embodiments, for example, the process may further comprise one or more of the following steps: (1) repeating the protection step and the pH adjustment step (if present); (2) a purge step prior to the deprotecting step; and (3) a buffer wash step prior to the drying step. In another embodiment, the process of the invention comprises (a) a first protection step, (b) a second protection step, (c) a filtration step, (d) an solvent extraction/separation step, (e) a buffer wash step, (f) a water reduction step; (g) a third protection step, (h) a concentration step, (i) a quaternization step, (j) a purge step, and (k) a hydrolysis step, whereby each of steps (a)-(k) are substantially as described above.

The sequence of steps for the preparation of naltrexone methobromide in accordance with certain of the preferred embodiments of the process of the present invention are described above. Advantageously, these steps lead to the conversion of naltrexone base to naltrexone methobromide in high yield, with high stereoselectivity for the R-isomer (relative to the nitrogen atom) over the S-isomer (relative to the nitrogen atom) of naltrexone methobromide and relatively low levels of the C(3)-O-methyl derivatives of naltrexone methobromide (in either of its R- or S-isomeric forms (i.e., R-MNTX and S-MNTX, respectively)), with R-MNTX and S-MNTX corresponding to the following structures:

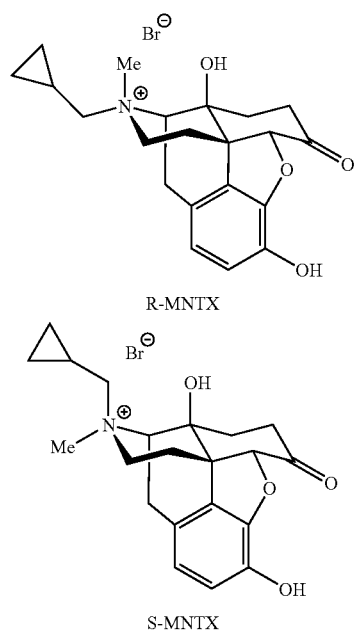

and the C(3)-O-methyl derivatives of R-MNTX and S-MNTX corresponding to the above structures with the phenolic C(3)-hydroxy group being replaced with a C(3)-O-methyl group. For example, the reaction product mixture will typically contain at least 70% (w/w) of R-naltrexone methobromide, at least 1% (w/w) of S-naltrexone methobromide, at least 1% (w/w) naltrexone, but no more than 0.2% (w/w) of C(3)-O-methyl derivative of naltrexone methobromide (in each of its isomeric forms), based upon the combined weight of the R-naltrexone methobromide, S-naltrexone methobromide, C(3)-O-methyl derivative of naltrexone methobromide, and naltrexone in the reaction product mixture (i.e., in the composition). More typically, the reaction product mixture typically includes from 2% to 5% (w/w) naltrexone, more typically 2% to 4% (w/w) naltrexone, based upon the combined weight of the R-naltrexone methobromide, S-naltrexone methobromide, C(3)-O-methyl derivative of naltrexone methobromide, and naltrexone in the reaction product mixture (i.e., in the composition). The reaction product mixture also typically includes from 5% to 10% (w/w) of S-naltrexone methobromide, more typically 6% to 7% (w/w), based upon the combined weight of the R-naltrexone methobromide, S-naltrexone methobromide, C(3)-O-methyl derivative of naltrexone methobromide, and naltrexone in the reaction product mixture. In a preferred embodiment, the reaction product mixture contains less than 0.15% (w/w) C(3)-O-methyl derivative of naltrexone methobromide (in each of its isomeric forms), more preferably less than 0.1% (w/w) C(3)-O-methyl derivative of naltrexone methobromide (in each of its isomeric forms), and still more preferably about 0.05% to 0.10% (w/w) C(3)-O-methyl derivative of naltrexone methobromide (in each of its isomeric forms), based upon the combined weight of the R-naltrexone methobromide, S-naltrexone methobromide, C(3)-O-methyl derivative of naltrexone methobromide, and naltrexone in the reaction product mixture (i.e., in the composition). The reaction product mixture preferably comprises at least 75% (w/w) R-naltrexone methobromide, more preferably at least 80% (w/w) R-naltrexone methobromide, and still more preferably at least 85% R-naltrexone methobromide, based upon the combined weight of the R-naltrexone methobromide, S-naltrexone methobromide, C(3)-O-methyl derivative of naltrexone methobromide, and naltrexone in the reaction product mixture (i.e., in the composition). Stated differently, in certain embodiments the weight ratio of the R-isomer of naltrexone methobromide to the C(3)-O-methyl derivative of naltrexone methobromide in the reaction product mixture is at least 150:1. More preferably in these embodiments, the weight ratio of the R-isomer of naltrexone methobromide to the C(3)-O-methyl derivative of naltrexone methobromide in the reaction product mixture is at least 250:1 (R-isomer:C(3)-O-methyl). Thus, for example, the weight ratio of the R-isomer of naltrexone methobromide to the C(3)-O-methyl derivative of naltrexone methobromide in the reaction product mixture may be at least 500:1, or at least 750:1, or at least 1,000:1 (R-isomer:C(3)-O-methyl). Similarly, the weight ratio of the S-isomer of naltrexone methobromide to the C(3)-O-methyl derivative of naltrexone methobromide in the reaction product mixture is typically at least 5:1 (S-isomer:C(3)-O-methyl). More typically, the weight ratio of S-isomer of naltrexone methobromide to the C(3)-O-methyl derivative of naltrexone methobromide in the reaction product mixture is at least 10:1 (S-isomer:C(3)-O-methyl). Still more typically, the weight ratio of S-isomer of naltrexone methobromide to the C(3)-O-methyl derivative of naltrexone methobromide in the reaction product mixture is at least 50:1 (S-isomer:C(3)-O-methyl). Finally, the weight ratio of naltrexone to C(3)-O-methyl derivative of naltrexone methobromide in the reaction product mixture is typically at least 5:1 (naltrexone:C(3)-O-methyl). More typically, the weight ratio of naltrexone to the C(3)-O-methyl derivative of naltrexone methobromide in the reaction product mixture is at least 10:1 (naltrexone:C(3)-O-methyl). Still more typically, the weight ratio of naltrexone to the C(3)-O-methyl derivative of naltrexone methobromide in the reaction product mixture is at least 50:1 (naltrexone:C(3)-O-methyl). In combination, in one embodiment the weight ratio of R-isomer of naltrexone methobromide to the C(3)-O-methyl derivative of naltrexone methobromide in the reaction product mixture is at least 150:1 (R-isomer:C(3)-O-methyl), the weight ratio of S-isomer of naltrexone methobromide to the C(3)-O-methyl derivative of naltrexone methobromide in the reaction product mixture is at least 5:1 (S-isomer:C(3)-O-methyl), and the weight ratio of naltrexone to C(3)-O-methyl derivative of naltrexone methobromide in the reaction product mixture is at least 5:1 (naltrexone:C(3)-O-methyl). More typically, the weight ratio of R-isomer of naltrexone methobromide to the C(3)-O-methyl derivative of naltrexone methobromide in the reaction product mixture is at least 250:1 (R-isomer:C(3)-O-methyl), the weight ratio of S-isomer of naltrexone methobromide to the C(3)-O-methyl derivative of naltrexone methobromide in the reaction product mixture is at least 10:1 (S-isomer:C(3)-O-methyl), and the weight ratio of naltrexone to C(3)-O-methyl derivative of naltrexone methobromide in the reaction product mixture is at least 5:1 (naltrexone:C(3)-O-methyl). Still more typically, the weight ratio of R-isomer of naltrexone methobromide to the C(3)-O-methyl derivative of naltrexone methobromide in the reaction product mixture is at least 500:1 (R-isomer:C(3)-O-methyl), the weight ratio of S-isomer of naltrexone methobromide to the C(3)-O-methyl derivative of naltrexone methobromide in the reaction product mixture is at least 50:1 (S-isomer:C(3)-O-methyl), and the weight ratio of naltrexone to C(3)-O-methyl derivative of naltrexone methobromide in the reaction product mixture is at least 5:1 (naltrexone:C(3)-O-methyl).

The final reaction product mixture is generally in the form of a solution or a slurry (which may include precipitated material) containing the above-described species. Because the reaction product mixture (e.g., the slurry or the solution) contains such low levels of C(3)-O-methyl derivative of naltrexone methobromide, purification steps are simplified. Thus, a crystallization product obtained from the reaction product mixture will contain relatively low levels of the C(3)-O-methyl derivative of naltrexone methobromide relative to R-naltrexone methobromide, S-naltrexone methobromide, and naltrexone. For example, the crystallization product will contain no more than 0.25% (w/w) of C(3)-O-methyl derivative of naltrexone methobromide (in each of its isomeric forms), based upon the combined weight of the R-naltrexone methobromide, S-naltrexone methobromide, C(3)-O-methyl derivative of naltrexone methobromide, and naltrexone in the crystallization product (i.e., in the composition). More typically, the crystallization product typically includes from 0.25% to 1% (w/w) naltrexone, more typically 0.5% to 0.75% (w/w) naltrexone, based upon the combined weight of the R-naltrexone methobromide, S-naltrexone methobromide, C(3)-O-methyl derivative of naltrexone methobromide, and naltrexone in the crystallization product (i.e., in the composition). The crystallization product also typically includes from 1% to 2% (w/w) of S-isomer of naltrexone methobromide, more typically 1% to 1.5% (w/w), based upon the combined weight of the R-naltrexone methobromide, S-naltrexone methobromide, C(3)-O-methyl derivative of naltrexone methobromide, and naltrexone in the crystallization product. In a preferred embodiment, the crystallization product contains less than 0.15% (w/w) C(3)-O-methyl derivative of naltrexone methobromide (in each of its isomeric forms), more preferably less than 0.1% (w/w) C(3)-O-methyl derivative of naltrexone methobromide (in each of its isomeric forms), and still more preferably about 0.05% to 0.10% (w/w) C(3)-O-methyl derivative of naltrexone methobromide (in each of its isomeric forms), based upon the combined weight of the R-naltrexone methobromide, S-naltrexone methobromide, C(3)-O-methyl derivative of naltrexone methobromide, and naltrexone in the crystallization product (i.e., in the composition). Stated differently, in certain embodiments the weight ratio of the R-isomer of naltrexone methobromide to the C(3)-O-methyl derivative of naltrexone methobromide in the crystallization product is at least 150:1 (R-isomer:C(3)-O-methyl). More preferably in these embodiments, the weight ratio of the R-isomer of naltrexone methobromide to the C(3)-O-methyl derivative of naltrexone methobromide in the crystallization product is at least 250:1 (R-isomer:C(3)-O-methyl). Thus, for example, the weight ratio of the R-isomer of naltrexone methobromide to the C(3)-O-methyl derivative of naltrexone methobromide in the crystallization product may be at least 500:1, or at least 750:1, or at least 1,000:1 (R-isomer:C(3)-O-methyl). Similarly, the weight ratio of the S-isomer of naltrexone methobromide to the C(3)-O-methyl derivative of naltrexone methobromide in the crystallization product is typically at least 2:1 (S-isomer:C(3)-O- methyl). More typically, the weight ratio of S-isomer of naltrexone methobromide to the C(3)-O-methyl derivative of naltrexone methobromide in the crystallization product is at least 5:1 (S-isomer:C(3)-O-methyl). Still more typically, the weight ratio of S-isomer of naltrexone methobromide to the C(3)-O-methyl derivative of naltrexone methobromide in the crystallization product is at least 10:1 (S-isomer:C(3)-O-methyl). Still more typically, the weight ratio of S-isomer of naltrexone methobromide to the C(3)-O-methyl derivative of naltrexone methobromide in the crystallization product is at least 15:1 (S-isomer:C(3)-O-methyl). Finally, the weight ratio of naltrexone to C(3)-O-methyl derivative of naltrexone methobromide in the crystallization product is typically at least 2:1 (naltrexone:C(3)-O-methyl). More typically, the weight ratio of naltrexone to the C(3)-O-methyl derivative of naltrexone methobromide in the crystallization product is at least 5:1 (naltrexone:C(3)-O-methyl). Still more typically, the weight ratio of naltrexone to the C(3)-O-methyl derivative of naltrexone methobromide in the crystallization product is at least 10:1 (naltrexone:C(3)-O-methyl). In combination, in one embodiment the weight ratio of R-isomer of naltrexone methobromide to the C(3)-O-methyl derivative of naltrexone methobromide in the crystallization product is at least 150:1 (R-isomer:C(3)-O-methyl), the weight ratio of S-isomer of naltrexone methobromide to the C(3)-O-methyl derivative of naltrexone methobromide in the crystallization product is at least 2:1 (S-isomer:C(3)-O-methyl), and the weight ratio of naltrexone to C(3)-O-methyl derivative of naltrexone methobromide in the crystallization product is at least 2:1 (naltrexone:C(3)-O-methyl). More typically, the weight ratio of R-isomer of naltrexone methobromide to the C(3)-O-methyl derivative of naltrexone methobromide in the crystallization product is at least 250:1 (R-isomer:C(3)-O-methyl), the weight ratio of S-isomer of naltrexone methobromide to the C(3)-O-methyl derivative of naltrexone methobromide in the crystallization product is at least 5:1 (S-isomer:C(3)-O-methyl), and the weight ratio of naltrexone to C(3)-O-methyl derivative of naltrexone methobromide in the crystallization product is at least 2:1 (naltrexone:C(3)-O-methyl). Still more typically, the weight ratio of R-isomer of naltrexone methobromide to the C(3)-O-methyl derivative of naltrexone methobromide in the crystallization product is at least 500:1 (R-isomer:C(3)-O-methyl), the weight ratio of S-isomer of naltrexone methobromide to the C(3)-O-methyl derivative of naltrexone methobromide in the crystallization product is at least 10:1 (S-isomer:C(3)-O-methyl), and the weight ratio of naltrexone to C(3)-O-methyl derivative of naltrexone methobromide in the crystallization product is at least 2:1 (naltrexone:C(3)-O-methyl).

Similarly, the process of the present invention may be used when the desired product is S-naltrexone methobromide. In this embodiment, however, oxymorphone is used instead of naltrexone as the substrate and the nitrogen atom of the substrate is alkylated with a cyclopropylmethyl alkylating agent such as cyclopropylmethylbromide. To minimize the formation of the corresponding C(3)-O-cyclopropylmethyl-S-naltrexone methobromide, the C(3)-hydroxy group of oxymorphone may be protected with a hydroxy protecting group during the cyclopropylmethylation reaction as otherwise described herein for the N-methylation of naltrexone and N-alkylation of other morphinan alkaloid substrates corresponding to Formula 1, 2, 3, 4, 11, 22, 222, etc. For example, the C(3)-hydroxy group of oxymorphone may be protected with an acetyl group as otherwise described in connection with the protection of the C(3)-hydroxy group of naltrexone in the synthesis of R-naltrexone methobromide and the C(3)-hydroxy protected oxymorphone substrate is N-alkylated using a cyclopropylmethyl alkylating agent as otherwise described in connection with the N-methylation of naltrexone in the synthesis of R-naltrexone methobromide. Advantageously, these steps lead to the conversion of oxymorphone base to naltrexone methobromide in high yield, with high stereoselectivity for the S-isomer (relative to the nitrogen atom) over the R-isomer (relative to the nitrogen atom) of naltrexone methobromide and relatively low levels of the C(3)-O-cyclopropylmethyl derivatives of naltrexone methobromide in either of its R- or S-isomeric forms (i.e., R-MNTX and S-MNTX, respectively). For example, the reaction product mixture will typically contain at least 70% (w/w) of S-naltrexone methobromide, at least 1% (w/w) of R-naltrexone methobromide, at least 1% (w/w) oxymorphone, but no more than 0.25% (w/w) of C(3)-O-cyclopropylmethyl derivative of naltrexone methobromide (in each of its isomeric forms), based upon the combined weight of the R-naltrexone methobromide, S-naltrexone methobromide, C(3)-O-cyclopropylmethyl derivative of naltrexone methobromide, and oxymorphone in the reaction product mixture (i.e., in the composition). More typically, the reaction product mixture typically includes from 2% to 5% (w/w) oxymorphone, more typically 2% to 4% (w/w) oxymorphone, based upon the combined weight of the R-naltrexone methobromide, S-naltrexone methobromide, C(3)-O-cyclopropylmethyl derivative of naltrexone methobromide, and oxymorphone in the reaction product mixture (i.e., in the composition). The reaction product mixture also typically includes from 5% to 10% (w/w) of R-naltrexone methobromide, more typically 6% to 7% (w/w), based upon the combined weight of the R-naltrexone methobromide, S-naltrexone methobromide, C(3)-O-cyclopropylmethyl derivative of naltrexone methobromide, and oxymorphone in the reaction product mixture. In a preferred embodiment, the reaction product mixture contains less than 0.15% (w/w) C(3)-O-cyclopropylmethyl derivative of naltrexone methobromide (in each of its isomeric forms), more preferably less than 0.1% (w/w) C(3)-O-cyclopropylmethyl derivative of naltrexone methobromide (in each of its isomeric forms), and still more preferably about 0.05% to 0.10% (w/w) C(3)-O-cyclopropylmethyl derivative of naltrexone methobromide (in each of its isomeric forms), based upon the combined weight of the R-naltrexone methobromide, S-naltrexone methobromide, C(3)-O-cyclopropylmethyl derivative of naltrexone methobromide, and oxymorphone in the reaction product mixture (i.e., in the composition). The reaction product mixture preferably comprises at least 75% (w/w) S-naltrexone methobromide, more preferably at least 80% (w/w) S-naltrexone methobromide, and still more preferably at least 85% S-naltrexone methobromide, based upon the combined weight of the R-naltrexone methobromide, S-naltrexone methobromide, C(3)-O-cyclopropylmethyl derivative of naltrexone methobromide, and oxymorphone in the reaction product mixture (i.e., in the composition). Stated differently, in certain embodiments the weight ratio of the S-isomer of naltrexone methobromide to the C(3)-O-cyclopropylmethyl derivative of naltrexone methobromide in the reaction product mixture is at least 150:1. More preferably in these embodiments, the weight ratio of the S-isomer of naltrexone methobromide to the C(3)-O-cyclopropylmethyl derivative of naltrexone methobromide in the reaction product mixture is at least 250:1 (S-isomer:C(3)-O-cyclopropylmethyl). Thus, for example, the weight ratio of the S-isomer of naltrexone methobromide to the C(3)-O-cyclopropylmethyl derivative of naltrexone methobromide in the reaction product mixture may be at least 500:1, or at least 750:1, or at least 1,000:1 (S-isomer:C(3)-O-cyclopropylmethyl). Similarly, the weight ratio of the R-isomer of naltrexone methobromide to the C(3)-O-cyclopropylmethyl derivative of naltrexone methobromide in the reaction product mixture is typically at least 5:1 (R-isomer:C(3)-O-cyclopropylmethyl). More typically, the weight ratio of R-isomer of naltrexone methobromide to the C(3)-O-cyclopropylmethyl derivative of naltrexone methobromide in the reaction product mixture is at least 10:1 (R-isomer:C(3)-O-cyclopropylmethyl). Still more typically, the weight ratio of R-isomer of naltrexone methobromide to the C(3)-O-cyclopropylmethyl derivative of naltrexone methobromide in the reaction product mixture is at least 50:1 (R-isomer:C(3)-O-cyclopropylmethyl). Finally, the weight ratio of oxymorphone to C(3)-O-cyclopropylmethyl derivative of naltrexone methobromide in the reaction product mixture is typically at least 5:1 (oxymorphone:C(3)-O-cyclopropylmethyl). More typically, the weight ratio of oxymorphone to the C(3)-O-cyclopropylmethyl derivative of naltrexone methobromide in the reaction product mixture is at least 10:1 (oxymorphone:C(3)-O-cyclopropylmethyl). Still more typically, the weight ratio of oxymorphone to the C(3)-O-cyclopropylmethyl derivative of naltrexone methobromide in the reaction product mixture is at least 50:1 (oxymorphone:C(3)-O-cyclopropylmethyl) In combination, in one embodiment the weight ratio of S-isomer of naltrexone methobromide to the C(3)-O-cyclopropylmethyl derivative of naltrexone methobromide in the reaction product mixture is at least 150:1 (S-isomer:C(3)-O-cyclopropylmethyl), the weight ratio of R-isomer of naltrexone methobromide to the C(3)-O-cyclopropylmethyl derivative of naltrexone methobromide in the reaction product mixture is at least 5:1 (R-isomer:C(3)-O-cyclopropylmethyl), and the weight ratio of oxymorphone to C(3)-O-cyclopropylmethyl derivative of naltrexone methobromide in the reaction product mixture is at least 5:1 (oxymorphone:C(3)-O-cyclopropylmethyl). More typically, the weight ratio of S-isomer of naltrexone methobromide to the C(3)-O-cyclopropylmethyl derivative of naltrexone methobromide in the reaction product mixture is at least 250:1 (S-isomer:C(3)-O-cyclopropylmethyl), the weight ratio of R-isomer of naltrexone methobromide to the C(3)-O-cyclopropylmethyl derivative of naltrexone methobromide in the reaction product mixture is at least 10:1 (R-isomer:C(3)-O-cyclopropylmethyl), and the weight ratio of oxymorphone to C(3)-O-cyclopropylmethyl derivative of naltrexone methobromide in the reaction product mixture is at least 5:1 (oxymorphone:C(3)-O-cyclopropylmethyl). Still more typically, the weight ratio of S-isomer of naltrexone methobromide to the C(3)-O-cyclopropylmethyl derivative of naltrexone methobromide in the reaction product mixture is at least 500:1 (S-isomer:C(3)-O-cyclopropylmethyl), the weight ratio of R-isomer of naltrexone methobromide to the C(3)-O-cyclopropylmethyl derivative of naltrexone methobromide in the reaction product mixture is at least 50:1 (R-isomer:C(3)-O-cyclopropylmethyl), and the weight ratio of oxymorphone to C(3)-O-cyclopropylmethyl derivative of naltrexone methobromide in the reaction product mixture is at least 5:1 (oxymorphone:C(3)-O-cyclopropylmethyl).

The final reaction product mixture is generally in the form of a solution or a slurry (which may include precipitated material) containing the above-described species. Because the reaction product mixture (e.g., the slurry or the solution) contains such low levels of C(3)-O-cyclopropylmethyl derivative of naltrexone methobromide, purification steps are simplified. Thus, a crystallization product obtained from the reaction product mixture will contain relatively low levels of the C(3)-O-cyclopropylmethyl derivative of naltrexone methobromide relative to R-naltrexone methobromide, S-naltrexone methobromide, and oxymorphone. For example, the crystallization product will typically contain no more than 0.25% (w/w) of C(3)-O-cyclopropylmethyl derivative of naltrexone methobromide (in each of its isomeric forms), based upon the combined weight of the R-naltrexone methobromide, S-naltrexone methobromide, C(3)-O-cyclopropylmethyl derivative of naltrexone methobromide, and oxymorphone in the crystallization product (i.e., in the composition). More typically, the crystallization product typically includes from 0.25% to 1% (w/w) oxymorphone, more typically 0.5% to 0.75% (w/w) oxymorphone, based upon the combined weight of the R-naltrexone methobromide, S-naltrexone methobromide, C(3)-O-cyclopropylmethyl derivative of naltrexone methobromide, and oxymorphone in the crystallization product (i.e., in the composition). The crystallization product also typically includes from 1% to 2% (w/w) of R-isomer of naltrexone methobromide, more typically 1% to 1.5% (w/w), based upon the combined weight of the R-naltrexone methobromide, S-naltrexone methobromide, C(3)-O-cyclopropylmethyl derivative of naltrexone methobromide, and oxymorphone in the crystallization product. In a preferred embodiment, the crystallization product contains less than 0.15% (w/w) C(3)-O-cyclopropylmethyl derivative of naltrexone methobromide (in each of its isomeric forms), more preferably less than 0.1% (w/w) C(3)-O-cyclopropylmethyl derivative of naltrexone methobromide (in each of its isomeric forms), and still more preferably about 0.05% to 0.10% (w/w) C(3)-O-cyclopropylmethyl derivative of naltrexone methobromide (in each of its isomeric forms), based upon the combined weight of the R-naltrexone methobromide, S-naltrexone methobromide, C(3)-O-cyclopropylmethyl derivative of naltrexone methobromide, and oxymorphone in the crystallization product (i.e., in the composition). Stated differently, in certain embodiments the weight ratio of the S-isomer of naltrexone methobromide to the C(3)-O-cyclopropylmethyl derivative of naltrexone methobromide in the crystallization product is at least 150:1 (S-isomer:C(3)-O-cyclopropylmethyl). More preferably in these embodiments, the weight ratio of the S-isomer of naltrexone methobromide to the C(3)-O-cyclopropylmethyl derivative of naltrexone methobromide in the crystallization product is at least 250:1 (S-isomer:C(3)-O-cyclopropylmethyl). Thus, for example, the weight ratio of the S-isomer of naltrexone methobromide to the C(3)-O-cyclopropylmethyl derivative of naltrexone methobromide in the crystallization product may be at least 500:1, or at least 750:1, or at least 1,000:1 (R-isomer:C(3)-O-cyclopropylmethyl). Similarly, the weight ratio of the R-isomer of naltrexone methobromide to the C(3)-O-cyclopropylmethyl derivative of naltrexone methobromide in the crystallization product is typically at least 2:1 (R-isomer:C(3)-O-cyclopropylmethyl). More typically, the weight ratio of R-isomer of naltrexone methobromide to the C(3)-O-cyclopropylmethyl derivative of naltrexone methobromide in the crystallization product is at least 5:1 (R-isomer:C(3)-O-cyclopropylmethyl). Still more typically, the weight ratio of R-isomer of naltrexone methobromide to the C(3)-O-cyclopropylmethyl derivative of naltrexone methobromide in the crystallization product is at least 10:1 (R-isomer:C(3)-O-cyclopropylmethyl). Still more typically, the weight ratio of R-isomer of naltrexone methobromide to the C(3)-O-cyclopropylmethyl derivative of naltrexone methobromide in the crystallization product is at least 15:1 (R-isomer:C(3)-O-cyclopropylmethyl). Finally, the weight ratio of oxymorphone to C(3)-O-cyclopropylmethyl derivative of naltrexone methobromide in the crystallization product is typically at least 2:1 (oxymorphone:C(3)-O-cyclopropylmethyl). More typically, the weight ratio of oxymorphone to the C(3)-O-cyclopropylmethyl derivative of naltrexone methobromide in the crystallization product is at least 5:1 (oxymorphone:C(3)-O-cyclopropylmethyl). Still more typically, the weight ratio of oxymorphone to the C(3)-O-cyclopropylmethyl derivative of naltrexone methobromide in the crystallization product is at least 10:1 (oxymorphone:C(3)-O-cyclopropylmethyl). In combination, in one embodiment the weight ratio of S-isomer of naltrexone methobromide to the C(3)-O-cyclopropylmethyl derivative of naltrexone methobromide in the crystallization product is at least 150:1 (S-isomer:C(3)-O-cyclopropylmethyl), the weight ratio of R-isomer of naltrexone methobromide to the C(3)-O-cyclopropylmethyl derivative of naltrexone methobromide in the crystallization product is at least 2:1 (R-isomer:C(3)-O-cyclopropylmethyl), and the weight ratio of oxymorphone to C(3)-O-cyclopropylmethyl derivative of naltrexone methobromide in the crystallization product is at least 2:1 (oxymorphone:C(3)-O-cyclopropylmethyl). More typically, the weight ratio of S-isomer of naltrexone methobromide to the C(3)-O-cyclopropylmethyl derivative of naltrexone methobromide in the crystallization product is at least 250:1 (S-isomer:C(3)-O-cyclopropylmethyl), the weight ratio of R-isomer of naltrexone methobromide to the C(3)-O-cyclopropylmethyl derivative of naltrexone methobromide in the crystallization product is at least 5:1 (R-isomer:C(3)-O-cyclopropylmethyl), and the weight ratio of oxymorphone to C(3)-O-cyclopropylmethyl derivative of naltrexone methobromide in the crystallization product is at least 2:1 (oxymorphone:C(3)-O-cyclopropylmethyl). Still more typically, the weight ratio of S-isomer of naltrexone methobromide to the C(3)-O-cyclopropylmethyl derivative of naltrexone methobromide in the crystallization product is at least 500:1 (S-isomer:C(3)-O-cyclopropylmethyl), the weight ratio of R-isomer of naltrexone methobromide to the C(3)-O-cyclopropylmethyl derivative of naltrexone methobromide in the crystallization product is at least 10:1 (R-isomer:C(3)-O-cyclopropylmethyl), and the weight ratio of oxymorphone to C(3)-O-cyclopropylmethyl derivative of naltrexone methobromide in the crystallization product is at least 2:1 (oxymorphone:C(3)-O-cyclopropylmethyl).

Viewed more generally, purification of the reaction product mixture to a crude product from the synthesis described above yields N-alkyl product of about 98% purity; assessed by HPLC relative to an analytical standard. The treatment of the protection and quaternization reaction mixtures according to the various processes and embodiments described herein results in a significantly reduced concentration of C(3)-O-alkyl morphinan alkaloid impurity in the compositions of the invention. Compositions that may include the quaternized product(s) described above include both final product mixtures (i.e., the crude final product mixture, e.g., dissolved in a solution) and/or the final crystallized products (i.e., a solid comprising the quaternized product in a crystalline form). In a particular embodiment, the composition includes the final crude product mixture. In another particular embodiments the composition includes the final product mixture after a first crystallization.

Another aspect of the present invention, therefore, is a composition comprising a C(3)-hydroxy quaternary N-substituted morphinan alkaloid corresponding to Formula 11A and no more than 0.1% (w/w) of a C(3)-alkoxy alkaloid corresponding to Formula 11C, relative to the amount of the C(3)-hydroxy quaternary N-substituted morphinan alkaloid corresponding to Formula 11A in the composition, wherein the alkaloids corresponding to Formula 11A and Formula 11C have the structures:

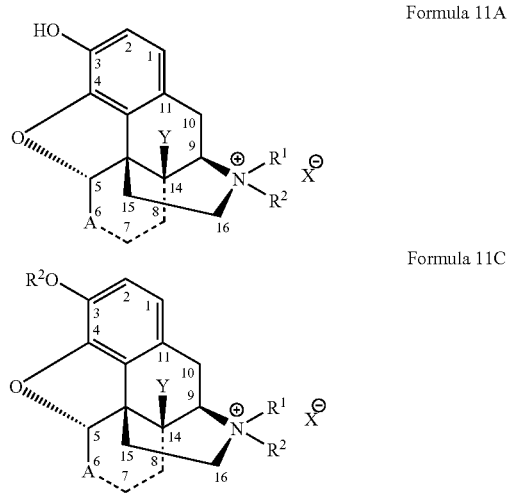

wherein
A is —C(O)—, —C(S)—, —C(=CH$_2$)—, —CH(A$_1$)- or —C(A$_1$)=,
A$_1$ is hydroxy, alkoxy, or acyloxy,
R$^1$ is hydrocarbyl or substituted hydrocarbyl;
R$^2$ is alkyl,
X$^1$ is a halide, sulfate, sulfonate, fluoroborate, fluorosulfonate, methylsulfate, ethylsulfate, trifluoromethanesulfonate, hexachloroantimonate, hexafluorophosphate, or tetrafluoroborate;
Y, if present, is hydrogen, hydroxy, protected hydroxy, alkoxy, or acyloxy, and
the dashed lines between the carbon atoms at positions 6 and 7, 7 and 8, and 8 and 14, respectively, represent (i) carbon-carbon single bonds; (ii) carbon-carbon single bonds between positions 6 and 7 and between positions 8 and 14, and a double bond between positions 7 and 8; or (iii) conjugated carbon-carbon double bonds between positions 6 and 7 and positions 8 and 14, with the proviso that Y is not present if there is a double bond between the carbons at positions 8 and 14.

As noted above, the compositions of the invention may include the crude final product mixtures (i.e., prior to any crystallization steps), the final product mixture after an initial crystallization, or the final crystallized active pharmaceutical ingredient (e.g., that this in final form). The processes of the present invention are particularly advantageous in that the presence of undesirable impurities and other species is significantly reduced at the crude final product mixture stage, prior to any crystallization. Subsequent crystallization steps may serve to further reduce the levels of such species below their already desirably low levels. In one embodiment, the C(3)-hydroxy quaternary N-substituted morphinan alkaloid present in the composition is naltrexone methobromide.

As noted above, the composition includes no more than about 0.1% of a C(3)-O-alkyl quaternary or tertiary N-substituted morphinan alkaloid impurity, relative to the total alkaloid content. For example, the composition may include less than about 0.05% of a C(3)-O-alkyl quaternary or tertiary N-substituted morphinan alkaloid impurity, relative to the total alkaloid content. Preferably, the composition includes no more than about 0.01% of a C(3)-Q-alkyl quaternary or tertiary N-substituted morphinan alkaloid impurity, relative to the total alkaloid content. For example, the composition may include less than about 0.005% of a C(3)-O-alkyl quaternary or tertiary N-substituted morphinan alkaloid impurity, relative to the total alkaloid content. More preferably, the composition includes no more than about 0.001% of a C(3)-O-alkyl quaternary or tertiary N-substituted morphinan alkaloid impurity, relative to the total alkaloid content. For example, the composition may include less than about 0.0005% of a C(3)-O-alkyl quaternary or tertiary N-substituted morphinan alkaloid impurity, relative to the total alkaloid content. Still more preferably, no detectable amount of a C(3)-O-alkyl quaternary or tertiary N-substituted morphinan alkaloid impurity is present in the composition.

Definitions

As used herein, "Ac" means acetyl, "Bn" means benzyl, "Bs" means brosyl, "Bz" means benzoyl, "Ms" means mesyl, "THP" means tetrahydropyranyl, and "Ts" means tosyl.

The term "anhydrous solvent" as used herein refers to solvents containing less than 0.5% by weight water, preferably maintained and handled under nitrogen gas during a reaction.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, tertiary amino, amido, nitro, cyano, ketals, acetals, esters and ethers.

Unless otherwise indicated, the alkyl groups described herein are preferably lower alkyl containing from one to eight carbon atoms in the principal chain. They may be straight or branched chain or cyclic and include methyl, ethyl, propyl, isopropyl, allyl, benzyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The terms "halogen" or "halo" as used herein alone or as part of another group refer to chlorine, bromine, fluorine, and iodine.

The term "halide" refers to fluoride, chloride, bromide, or iodide ions.

The term "narcotics" as used herein refers to drugs that depress the central nervous system and relieve pain when used in moderate doses.

The term "opioid" as used herein refers to non-opium-derived (synthetic or naturally occurring) narcotics that act on the central nervous system to decrease the sensation of pain.

Having described the invention in detail, it will be apparent that modifications and variations are possible without departing from the scope of the invention defined in the appended claims.

The following non-limiting examples are provided to further illustrate the present invention.

Reagents

A dehydrated naltrexone base was used in experiments that did not require phenolic C(3)-hydroxide protection. This base was prepared from naltrexone hydrochloride which was dried under vacuum until the water content was about 2% by Karl-Fischer analysis. A hydrated naltrexone base (the dihydrate) was used in the experiments that require protection of the phenolic hydroxide.

A bottle of hydrogen bromide (HBr) was cooled to −70° C. and 1-methyl-2-pyrrolidinone (N-methylpyrrolidone; NMP) was cooled down to −20° C. HBr (13.01 g; 160 mmol) was added into the NMP (130 mL) and the solution was allowed to warm to room temperature. The solution was then diluted with NMP to 160.0 mL to form a 1N solution of HBr in NMP (HBr/NMP).

A bottle containing methyl bromide (MeBr; b.p. 4° C.) was cooled down to −10° C. MeBr (50.00 mL) was poured out and weighed (88.53 g; d=1.77 g/mL). The methyl bromide was added into a pre-cooled bottle containing 1-Methyl-2-Pyrrolidinone (NMP) {50.00 mL; 54.39 g, −10° C.} to form approximately 100 mL solution at −10° C. (MeBr/NMP).

COMPARATIVE EXAMPLE A

Synthesis of Naltrexone Methobromide

A comparative N-methylation was performed, by addition of 1.5 equiv. MeBr/NMP to a bulk suspension of 12.5 Kg anhydrous naltrexone in NMP (1.5 volume equivalents (vol. equiv.)) following the scaled-up version of the general procedure disclosed in Example 1 of WO 2004/043964 The yield of crude naltrexone methobromide product was 9.43 Kg. The product yield was 60.9 mol. % in Comparative Example A, and 12.6 mol. % of side products were produced.

Example 1

Synthesis of Naltrexone Methobromide: Slow Addition of MeBr 1-methyl-2-pyrrolidinone (N-methylpyrrolidinone, NMP, 150 mL) was added into a three-necked, 1000-mL flask and heated to 58° C. under a nitrogen flow. Naltrexone base (100.00 g, a solid, containing 2% water; 287 mmol) was added. The funnel was washed with 25 mL of NMP. The mixture remained a suspension after 1 hour of heating.

A 50-mL solution of MeBr/NMP (466 mmol MeBr) was transferred into a pre-cooled dropping funnel (−10° C.) equipped with a cooling system to maintain the MeBr at a temperature between −10° C. and 0° C. Nitrogen was passed over the top of the condenser. The MeBr/NMP solution was added drop-wise from the funnel into the naltrexone/NMP suspension over 30 minutes and the temperature increased over this time period up to 58° C. The resulting mixture was heated at about 55-58° C. for 20 minutes to form a solution and the heating was continued at about 65° C. with stirring under nitrogen for 12 hours. Solids started to form after 2 hours at 65° C. The reaction mixture was cooled to room temperature to yield a thick suspension, 250 mL of acetone was added, and the mixture was stirred for 1 hour and filtered. The solid was washed with two 25-mL aliquots of acetone and dried under vacuum at 55° C. to give 92.26 g of a crude product as a white solid. The combined filtrate and washes were collected (452 g of liquid) for recovery of unreacted naltrexone.

Example 2

Synthesis of Naltrexone Methobromide: Slow Addition of MeBr 1-methyl-2-pyrrolidinone (NMP, 50 mL) was added to a three-necked, 250-mL flask which was heated to 54° C. and blanketed under nitrogen. 40 g of naltrexone base, containing 2% water was added and the funnel was washed with 10 mL of NMP. The mixture remained as a suspension after 0.5 hour of heating.

A 20-mL solution of MeBr/NMP (93.2 mmol MeBr) was transferred into a pre-cooled dropping funnel (−10° C.) equipped with a cooling system to maintain MeBr at between −10 and 0° C. Nitrogen was introduced at the top of the water condenser (about 20° C.). A 10-mL portion of the MeBr/NMP solution was added drop-wise into the suspension over 15 minutes at about 56-58° C. The resulting mixture was heated at about 56-58° C. under nitrogen for another 30 minutes. Most of the solid substrate was dissolved at this point. The remaining MeBr/NMP solution was added drop-wise into the reaction mixture over a 10-minute period at about 56-58° C. and stirring was maintained at about 57° C. for another 10 minutes followed by further heating to about 63-65° C. for 12 hours. After this period, the suspension was cooled to room temperature and stirred for 4 hours. Ninety (90) mL of acetone was added to the reaction mixture and heat was released. The mixture was stirred for 1 hour allowed to cool to room temperature and then filtered. The solid was washed with four 10-mL aliquots of acetone and dried under vacuum at 55° C. for 19 hours to give 40.22 g of crude product as a white solid. The combined washes (mother liquor: 177.5 mL) were collected for recovery of unreacted naltrexone.

Example 3

Synthesis of Naltrexone Methobromide: Slow Addition of MeBr; and Substitution of Chloroform for Acetone 1-methyl-2-pyrrolidinone (NMP, 25 mL) was added into a three-necked 250-mL flask and heated to 57° C. under nitrogen. 20 g of naltrexone base (containing 2% water) was added via a funnel and the funnel was washed with 5 mL of NMP. The mixture remained as a suspension after heating for 30 minutes.

A 10-mL solution of MeBr/NMP (93.2 mmol MeBr) was transferred into a pre-cooled dropping funnel (−10° C.) equipped with a cooling system to maintain the MeBr solution at below 0° C. A nitrogen sweep was introduced at the top of the attached water-cooled condenser (about 20° C.) and about 7 mL of the MeBr/NMP solution was added drop-wise to the suspension over 15 minutes at about 56-58° C. The resulting mixture was heated at about 56-58° C. under nitrogen for 30 minutes by which time most of the solid was dissolved. The remaining MeBr/NMP solution was added drop-wise to the reaction mixture over 10 minutes at about 56-58° C. and stirring was continued for an additional 10 minutes followed by heating at about 63-65° C. under nitrogen for 12 hours. A precipitate formed after 2-3 hours. At the end of the 12-hour period, the suspension was cooled to room temperature and stirring was continued for an additional 4 hours.

To the reaction mixture was added 45 mL of $CHCl_3$. The addition was exothermic and the temperature of mixture rose to 35° C. from room temperature. The mixture was then allowed to cool to room temperature with stirring for 1 hour after which the solid suspension was separated by filtration, washed with three 10-mL portions of $CHCl_3$ and vacuum dried at 55° C. for 19 hours to yield 19.55 g of elude product as a white solid. The combined filtrate and washes were collected (mother liquor, 84.5 mL) for recovery of unreacted naltrexone base.

Example 4

Synthesis of Naltrexone Methobromide in Presence of HBr: Slow Addition of MeBr and Substitution of Chloroform for Acetone 1-methyl-2-pyrrolidinone (NMP, 33.3 mL) and 15 g of naltrexone base (containing 2% water) were added into a three-necked 250-mL flask under nitrogen. An 11.7 mL solution of 1.00N HBr/NMP and 14 mL of t-BuOH were added. The solution was heated to about 54° C., an extra 25.00 g of naltrexone base (containing 2% water) was added via a funnel, and the funnel was washed with 10 mL of NMP. The final mixture remained as a suspension after heating for 30 minutes.

A 20-mL aliquot of MeBr/NMP (186.4 mmol MeBr) was transferred into a pre-cooled dropping funnel (−10° C.) equipped with a cooling system to maintain the MeBr at below 0° C. Nitrogen was introduced at the top of the attached water-cooled condenser (about 20° C.). 13 mL of the MeBr/NMP solution was added drop-wise to the suspension over 15 minutes at about 55-57° C. The resulting mixture was heated at approximately 55-57° C. under nitrogen for another 30 minutes to form a clear solution. The remaining MeBr/NMP solution was added drop-wise to the reaction mixture over 10 minutes at approximately 55-57° C., stirred for an additional 10 minutes, then heated to approximately 61-63° C. for 19 hours. The resultant suspension was cooled to room temperature, stirred for 4 hours, and 90 mL of chloroform was added which resulted in heat release. After cooling to room temperature and stirring for approximately 1 hour, the solids were separated by filtration, washed with four 10-mL portions of chloroform, and dried under vacuum at about 55° C. for 19 hours. This afforded 38.58 g of crude product as a white solid.

The combined washes were collected (mother liquor, 166.5 mL) for recovery of unreacted naltrexone.

Discussion of the Results of Examples 1-4 and the Comparative Example

In each of the above examples, the components of the final reaction mixture were analyzed by HPLC and the results tabulated; see Tables 1 and 3, and Scheme 3. The identified components are grouped as follows:
(1) Nal-MeBr=naltrexone methobromide, desired product;
(2) Nal=naltrexone=recyclable starting material; and
(3) Other side products=Nal-MeBr-isomer, MeO-Nal, MeO-Nal-MeBr; not recyclable.

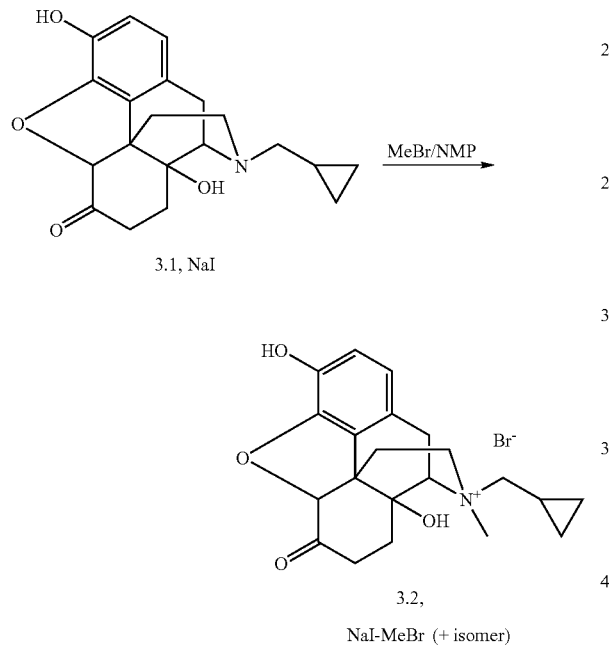

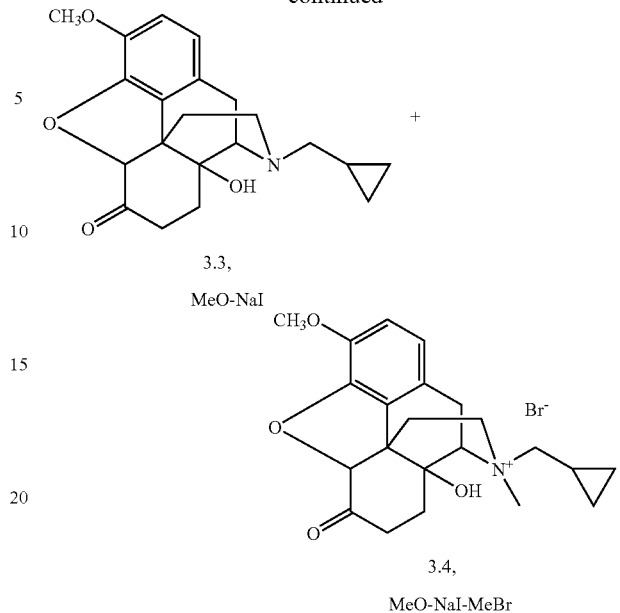

The data entered for Examples 1-3 in Table 3 indicate that slow addition of MeBr/NMP over 10-30 minutes increases the yield of naltrexone methobromide to about 68 to 79%.

The entry for Example 4 in Table 3 represents the effect of the addition of acid (0.1 equiv. HBr). Incorporation of this reagent increased the yield of the product (naltrexone methobromide) to about 77.5% and decreased the side products to about 5.1%. Addition of HBr suppresses the ionization of the C(3) hydroxide (phenolic hydroxide) of naltrexone to form Nal$^-$ (see Scheme 4) and thereby reduces the chemical reactivity of the C(3) hydroxide toward MeBr. Further, addition of a strong anhydrous acid (HBr) to the reaction system permits use of partially hydrated naltrexone (Naltrexone.2H$_2$O) as a starting material instead of anhydrous naltrexone thereby eliminating the processing costs associated with dehydration of naltrexone. Since an additional reaction step is required to prepare anhydrous naltrexone from the hydrate (Naltrexone.2H$_2$O), addition of HBr would reduce processing costs.

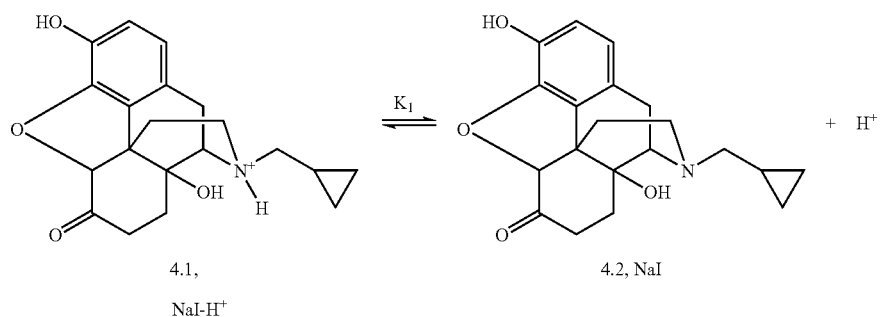

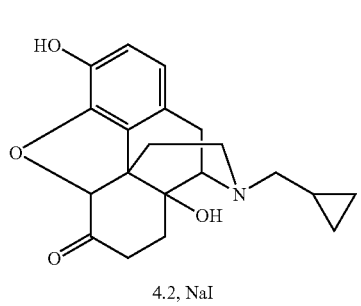
4.2, NaI

-continued

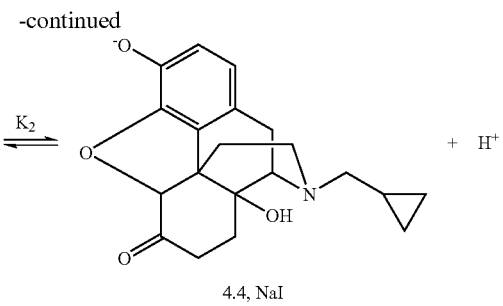
4.4, NaI

Approximately 13 mol. % of C(3)-O-methyl side products were realized in Comparative Example A. In Examples 1-3, the C(3)-O-methyl side products are reduced about 3-fold to 5-fold. In Example 4 which incorporated the process improvements of Examples 1-3, increases in the yield and purity of the quaternized product, naltrexone methobromide was observed (see summary in Table 2).

The procedures of Examples 1-3 differ from that of Comparative Example A by (i) slowing the addition of MeBr/NMP;
(ii) reducing the temperature of the MeBr/NMP (maintained at about 0° C. to −10° C. during addition) into the NMP solution of naltrexone (containing 2% water) at approximately 55-58° C.; and
(iii) extending the reaction period from 10 to 12 hours.

The processes of Examples 1-3 yielded a higher molar percentage of the product, naltrexone methobromide (Nal-MeBr) compared to the process of Comparative Example A. In Example 4, 0.1 equiv. of HBr was also added into the reaction mixture. The increased hydrogen ion (H$^+$) concentration was found to depress the formation of side products, e.g., O-methyl naltrexone and O-methyl naltrexone methobromide, thus improving the purity of the crude product.

TABLE 1

Yield of crude product

| Example No. | Nal. charged | KF* % | LOD** % | Crude Yield |
|---|---|---|---|---|
| Comp. A | 12.5 Kg | 0.61 | 0~0.2 | 9.43 Kg |
| 1 | 100.00 g | 1.22 | 0.04 | 92.26 g |
| 2 | 20.00 g | 3.06 | 0.07 | 18.90 g |
| 3 | 40.00 g | 1.13 | 0.06 | 35.92 g |
| 4 | 40.00 g | 1.18 | 0.12 | 37.56 g |

*KF is Karl-Fischer test for water.
**LOD is the weight loss on drying.

TABLE 2

Crude product quality*

| Example No. | Crude Yield | % Nal. MeBr | % Nal | % O-Methyl Nal |
|---|---|---|---|---|
| Comp A | 9.43 Kg | 90.26 | 2.63 | 6.0 |
| 1 | 92.26 g | 84.98 | 1.81 | 4.62 (area %) |
| 2 | 18.90 g | 96.7 | 2.10 | 4.70 (area %) |
| 3 | 35.92 g | 89.32 | 1.48 | 5.11 (area %) |
| 4 | 37.56 g | 97.36 | 2.65 | 1.57 (area %) |

*The data in Table 2 are wt./wt. % except O-Methyl Nal area % from HPLC analysis.

TABLE 3

Distribution of product and by-products

| Example No. | Mol. % Nal. MeBr* | Mol. % Nal** | Mol. % Others*** |
|---|---|---|---|
| Comp A | 60.9 | 26.5 | 12.6 |
| 1 | 68.3 | 14.8 | 16.9 |
| 2 | 79.0 | 10.3 | 10.7 |
| 3 | 75.1 | 9.7 | 15.2 |
| 4 | 77.5 | 17.4 | 5.1 |

*Nal. MeBr: naltrexone methobromide;
**Nal: naltrexone;
***O-methyl-Nal: C(3)-O-methyl-naltrexone.

Example 5

Synthesis of C(3)-Acetoxy Naltrexone

Deionized water (600 mL) and naltrexone base (90. g, 0.26 moles (mol)) were mixed in a 2-L, three-necked round bottomed flask equipped with a mechanical stirrer, addition funnel, and thermocouple. Toluene (300 mL) was added, the mixture was stirred under a nitrogen atmosphere for 5 minutes, and NaOH (0.26 mol) was then added as a 10% w/w aqueous solution via an addition funnel over a 10 minute period. A temperature increase from 21.5° C. to 22.6° C. was observed. The resulting solution was then stirred for 15 minutes (all solid dissolved) and acetic anhydride (29.61 g, 0.29 mol) was added over a 15-minute period and the temperature was increased to 27.1° C. The resulting mixture was then stirred for 15 minutes and the pH was adjusted from 6.55 to 10.15 with 10 wt. % solution of NaOH (24.2 g, 0.06 mol.). The mixture was stirred for 10 minutes, the layers were separated and the aqueous layer was extracted once with toluene (100 mL). The combined organic layers were then filtered through a Whatman Glass Microfibre Filter (GF/A, 90 mm) and the resulting filtrate was allowed to sit undisturbed for further separation of water. The residual water was removed, and C(3)-acetoxy naltrexone/toluene solution was obtained (459.8 g). The solution was concentrated under reduced pressure to afford an amber/yellow oil and then dissolved in NMP to prepare a 30.0 wt. % solution of the product.

Example 6

Synthesis of Naltrexone Methobromide

To a 1-L, 5-neck, jacketed pressure reactor equipped with a polished glass stirring shaft, mechanical stirrer, reflux condenser, pressure manifold, thermowell, and ⅛" ID MeBr addition line was added a solution of C(3)-acetoxy naltrexone in NMP (732.2 g of 30% wt/wt solution, 0.57 moles). Methyl bromide (107.9 g, 1.14 moles) was then added via a subsurface addition with vigorous stirring over a 1 hour period. The amount of MeBr added to the reactor was ascertained by a difference in the initial and final weights of a MeBr lecture bottle. During the addition, the temperature of the reaction mass increased from 20.8° C. to 32.9° C. (yellow solution) and a maximum pressure of 3-4 psi was observed. After the appropriate amount of MeBr was added, the reactor headspace was evacuated and repressurized with MeBr (to about 2 psi) twice before heating to 60° C. At 60° C., a pressure of 2-4 psi was observed. The reaction mixture was stirred overnight (15 hours) and no pressure was observed (a yellow solution resulted). Aqueous HBr (1.0 equiv, 0.57 moles, 96.58 g of 48 wt. %) was added slowly at 60° C. over a 30-minute period. The reactor was vented into NMP in order to trap gaseous methyl bromide that was generated during the HBr addition. During the addition, the reaction temperature increased to 63.7° C. The reaction temperature was then increased to 80° C. over a 1.5 hour period and the methyl bromide evolution ceased. The mixture was stirred at 80° C. for 2 hours and precipitation was observed. After 5 hours at 80° C., the slurry was analyzed by HPLC and a minor amount of C(3)-acetoxy naltrexone methobromide was observed (<0.5% by area) was observed. The mixture was then transferred to a 2-L three-neck round bottomed flask equipped with a glass stirring shaft, mechanical stirrer, reflux condenser, and thermocouple under a nitrogen atmosphere. The mixture was cooled to 56.2° C. and methanol (512.5 g, 1.0 wt equiv. based on the amount of NMP charged) was added quickly. The temperature decreased quickly to 41.2° C. and then increased to 42.5° C. upon crystallization of naltrexone methobromide. The slurry was then cooled to 29.7° C. over a 30 minute period and then to 5-10° C. in an ice bath. The slurry was stirred for 1 hour at 5-10° C., filtered, and the product was washed with cold methanol (319 mL, 1.45 mL/g C(3)-acetoxy naltrexone assuming 212.5 g naltrexone methobromide (85% overall yield)) to afford 236.1 g of a white solid. The crude product was analyzed by HPLC. This example was repeated two additional times and the results are summarized in Table 4. The HPLC assay data for the solid product is an average of two separate injections.

TABLE 4

Summary of Results: Example 6 - Synthesis of Naltrexone Methobromide.

| Run | 3-AcNal$^a$ (moles) | Hydrolysis Time (hours) | NalMeD$^a$ (wt. %) | NalMe$^a$ (wt. %) | Nal$^a$ (wt. %) | Yield (mole %) |
|---|---|---|---|---|---|---|
| 1 | 0.3915 | 25 | 1.47 | 86.54 | 0.49 | 87.2 |
| 2 | 0.4890 | 17 | 1.39 | 86.73 | 0.60 | 85.6 |
| 3 | 0.5729 | 5 | 1.25 | 87.98 | 0.57 | 83.1 |

$^a$3-AcNal = C(3)-Acetoxy Naltrexone, NalMeD = Naltrexone Methobromide Diastereomer, NalMe = Naltrexone Methobromide, Nal = Naltrexone Base.

Example 7

Recrystallization of Naltrexone Methobromide

A mixture of water (15.82 mL, 1.58 mL water/g naltrexone methobromide) and methanol (33.47 mL, 3.35 mL methanol/g naltrexone methobromide) were mixed and heated under a nitrogen atmosphere in a 100 mL three-necked round bottomed flask equipped with a glass stirring shaft, mechanical stirrer, reflux condenser, and thermocouple to 60° C., and solid naltrexone methobromide (10.00 g, 22.92 mmoles) was added. After 15 minutes, the solid dissolved and aqueous HBr (0.93 g of a 48% solution, 5.5 mmoles, 24 mol %) was added to obtain an aqueous methanol mixture comprised of 1.63 mL water/g naltrexone methobromide and 3.52 mL methanol/g naltrexone methobromide. The heating mantle was removed and the mixture was allowed to slowly cool to room temperature. Crystallization was observed at 48° C. The mixture was cooled to 25° C. over a period of 1 hour, then cooled to 5-10° C. in an ice bath, stirred for 2 hours, filtered, and the solid was washed with cold methanol (15 mL, 1.5 mL/g naltrexone methobromide). The solid was then dried on the Büchner funnel for 15 minutes to afford 10.84 g of naltrexone methobromide as a white solid contaminated with methanol. The product was analyzed by HPLC. The HPLC assay data for the solid product is an average of two separate injections. The results of several experiments are summarized in Table 5.

TABLE 5

Summary of Results: Example 7 - Naltrexone Methobromide Recrystallization

| Run | HBr (mol %) | Water (mL/g NalMe$^a$) | Methanol (mL/g NalMe) | NalMeD$^a$ (wt. %) | NalMe$^a$ (wt. %) | Nal$^a$ (wt. %) | 3-MeNalMe$^a$ (wt. %) | Recovery (mole %) |
|---|---|---|---|---|---|---|---|---|
| 1 | 12.0 | 1.81 | 3.52 | 0.30 | 93.53 | 0.08 | 0.07 | 87.4 |
| 2 | 18.0 | 1.72 | 3.71 | 0.35 | 86.45 | 0.12 | 0.06 | 95.4 |
| 3 | 24.0 | 1.81 | 3.89 | 0.36 | 94.21 | 0.14 | 0.08 | 87.0 |
| 4 | 12.0 | 1.63 | 3.52 | 0.37 | 85.32 | 0.14 | 0.06 | 93.3 |
| 5 | 18.0 | 1.72 | 3.71 | 0.31 | 93.45 | 0.12 | 0.07 | 88.3 |
| 6 | 12.0 | 1.81 | 3.89 | 0.31 | 80.92 | 0.12 | 0.06 | 91.1 |
| 7 | 24.0 | 1.81 | 3.52 | 0.32 | 93.59 | 0.12 | 0.08 | 87.7 |
| 8 | 24.0 | 1.63 | 3.52 | 0.40 | 90.23 | 0.15 | 0.07 | 96.0 |
| 9 | 12.0 | 1.63 | 3.89 | 0.31 | 91.10 | 0.12 | 0.07 | 84.9 |
| 10 | 24.0 | 1.63 | 3.89 | 0.31 | 88.81 | 0.12 | 0.06 | 92.8 |

$^a$NalMeD = Naltrexone Methobromide Diastereomer, NalMe = Naltrexone Methobromide, Nal = Naltrexone Base, 3-MeNalMe = C(3)-Methoxy Naltrexone Methobromide.

Example 8

Preparation of Methylnaltrexone Bromide

Methylnaltrexone bromide (R-MNTX). To a mixture of naltrexone base (110 Kg@100.0%, 323 moles) and USP Purified water (330 Kg, 3.00 Kg/Kg naltrexone base, 87 gal, 0.79 gal/Kg naltrexone base) was added 50% NaOH (25.7 Kg, 0.234 Kg/Kg naltrexone base). Toluene (288 Kg, 2.62 Kg/Kg naltrexone base) was added to the aqueous layer. The mixture was stirred and acetic anhydride (37.8 Kg, 0.344 kg/kg naltrexone base) was added. The resulting mixture was then stirred and the pH was adjusted to 9.5-10.5 with 50% NaOH (7.59 Kg, 0.069 Kg/Kg naltrexone base). Acetic anhydride (36.7 Kg, 0.030 Kg/Kg naltrexone base) was added and the mixture was stirred and the pH was adjusted to 9.5-10.5 with 50% NaOH (5.06 Kg, 0.046 Kg/Kg naltrexone base). The mixture was allowed to settle and the layers were separated. The aqueous layer was extracted with toluene (45.5 Kg, 0.414 Kg/Kg naltrexone base) and the layers were separated. The organic layers were combined and the aqueous layer was discarded. A pH 9.0, 0.375 M phosphate buffer solution (165 Kg, 1.5 Kg/Kg naltrexone base) was prepared by mixing 5.80 Kg of 85% $H_3PO_4$ (0.0527 Kg/Kg naltrexone base), 9.39 Kg 50% NaOH (0.0854 Kg/Kg naltrexone base), and 150 Kg DI water (1.36 Kg/Kg naltrexone base). The combined toluene layers were then washed with the pH 9.0 phosphate buffer (165 Kg, 1.5 Kg/Kg naltrexone base). The layers were separated and the toluene layer was concentrated. The vacuum was broken with nitrogen and acetic anhydride (330 g, 0.003 Kg/Kg naltrexone base) was added. The mixture was stirred at 50-55° C. Vacuum was again applied and remaining toluene was removed by distillation. The vacuum was broken with nitrogen and 1-methyl-2-pyrrolidinone (268 Kg, 2.44 Kg/Kg naltrexone base) was added. The mixture was stirred for 60 minutes and cooled to room temperature to afford a solution of 3-acetylnaltrexone in NMP. Methyl bromide (61.2 Kg, 0.556 Kg/Kg naltrexone base) was then added with vigorous stirring. The reaction mixture was stirred at 60-65° C. to afford a solution. Reaction completion was ascertained via HPLC analysis. A 33% HBr/HOAc (w/w) solution (19.8 Kg, 0.180 Kg/Kg naltrexone base) was added. The mixture was stirred at ~60° C. Aqueous 48% HBr (54.3 Kg, 0.494 Kg/Kg naltrexone base) was added at 60° C. The mixture was then stirred at ~80° C. and cooled to ~55° C. Methanol (288 Kg, 2.62 Kg/Kg naltrexone base) was added at ~55° C. and the slurry was cooled to 10° C., stirred at 5-10° C., filtered, and the product was washed with methanol (220 Kg, 2.0 Kg/Kg naltrexone base) to afford a white, crystalline solid. The purity of the crude methylnaltrexone bromide product was ascertained by an HPLC assay method and subsequent raw material charges for recrystallization were calculated employing the weight of the product on a 100% basis.

To a mixture of water (1.58 Kg/Kg methylnaltrexone bromide@100%) and methanol (2.78 Kg/Kg methylnaltrexone bromide@100%) was added crude methylnaltrexone bromide. The mixture was heated to 60-65° C. under a nitrogen atmosphere and a solution resulted. The solution was filtered and aqueous 48% HBr (0.094 kg/kg methylnaltrexone bromide@100%) was added. The mixture was cooled to 10° C., filtered, and the solid was washed with methanol (1.2 Kg/Kg methylnaltrexone bromide@100%). The product was dried at 70-75° C. to afford 100 Kg of a white crystalline solid.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and processes without departing from the scope of the invention, it is intended that all matter contained in the above descriptions shall be interpreted as illustrative and not in a limiting sense.

What is claimed is:

1. A composition comprising R-naltrexone methobromide, S-naltrexone methobromide, the C(3)-O-methyl derivative of naltrexone methobromide, and naltrexone wherein the composition contains at least 70% (w/w) of R-naltrexone methobromide, at least 1% of S-naltrexone methobromide, but no more than 0.2% (w/w) of the C(3)-O-methyl derivative of naltrexone methobromide, based upon the combined weight of the R-naltrexone methobromide, S-naltrexone methobromide, C(3)-O-methyl derivative of naltrexone methobromide, and naltrexone in the composition.

2. The composition of claim 1, the composition being in the form of a mixture with the weight ratio of S-naltrexone methobromide to C(3)-O-methyl derivative of naltrexone methobromide in the mixture being at least 10:1.

3. The composition of claim 2, wherein the mixture is in the form of a slurry or a solution.

4. The composition of claim 1, the composition being in the form of a mixture with the weight ratio of naltrexone to C(3)-O-methyl derivative of naltrexone methobromide in the mixture being at least 10:1.

5. The composition of claim 4, wherein the mixture is in the form of a slurry or a solution.

6. The composition of claim 2, wherein the composition contains no more than 0.1% (w/w) of the C(3)-O-methyl derivative of naltrexone methobromide, based upon the combined weight of the R-naltrexone methobromide, S-naltrexone methobromide, C(3)-O-methyl derivative of naltrexone methobromide, and naltrexone in the composition.

7. The composition of claim 1, the composition being in the form of a crystallized solid with the weight ratio of S-naltrexone methobromide to C(3)-O-methyl derivative of naltrexone methobromide in the crystallized solid being at least 10:1.

8. The composition of claim 1, the composition being in the form of a crystallized solid with the weight ratio of naltrexone to C(3)-O-methyl derivative of naltrexone methobromide in the crystallized solid being at least 10:1.

9. The composition of claim 7, wherein the composition contains no more than 0.1% (w/w) of the C(3)-O-methyl derivative of naltrexone methobromide, based upon the combined weight of the R-naltrexone methobromide, S-naltrexone methobromide, C(3)-O-methyl derivative of naltrexone methobromide, and naltrexone in the composition.

* * * * *